(12) United States Patent
Nishimoto et al.

(10) Patent No.: US 6,479,123 B2
(45) Date of Patent: Nov. 12, 2002

(54) DIPYRROMETHENE-METAL CHELATE COMPOUND AND OPTICAL RECORDING MEDIUM USING THEREOF

(75) Inventors: Taizo Nishimoto, Chiba (JP); Hisashi Tsukahara, Chiba (JP); Shinobu Inoue, Chiba (JP); Akira Ogiso, Chiba (JP); Tsutami Misawa, Chiba (JP); Tadashi Koike, Chiba (JP)

(73) Assignees: Mitsui Chemicals, Inc. (JP); Yamamoto Chemicals, Inc. (JP)

( * ) Notice: Subject to any disclaimer, the term of this patent is extended or adjusted under 35 U.S.C. 154(b) by 62 days.

(21) Appl. No.: 09/793,083

(22) Filed: Feb. 27, 2001

(65) Prior Publication Data

US 2002/0048645 A1 Apr. 25, 2002

(30) Foreign Application Priority Data

Feb. 28, 2000 (JP) .................................. 2000-051242
Nov. 17, 2000 (JP) .................................. 2000-351399

(51) Int. Cl.$^7$ ................................................. B32B 3/02
(52) U.S. Cl. ..................... 428/64.1; 428/64.4; 428/64.8; 430/270.16
(58) Field of Search .................... 428/64.1, 64.4, 428/64.8, 913; 430/270.14, 270.16, 495.1, 945; 369/283, 288

(56) References Cited

U.S. PATENT DOCUMENTS

5,948,593 A * 9/1999 Misawa .................. 430/270.16
6,162,520 A * 12/2000 Misawa ..................... 428/64.1

FOREIGN PATENT DOCUMENTS

EP        0 903 733 A2      3/1999
JP        11-302551 A1     11/1999

* cited by examiner

*Primary Examiner*—Elizabeth Mulvaney
(74) *Attorney, Agent, or Firm*—Burns, Doane, Swecker & Mathis, L.L.P.

(57) ABSTRACT

An optical recording medium comprising at least a recording layer and a reflecting layer on a substrate wherein the recording layer contains at least one dipyrromethene-metal chelate compound represented by general formula (1):

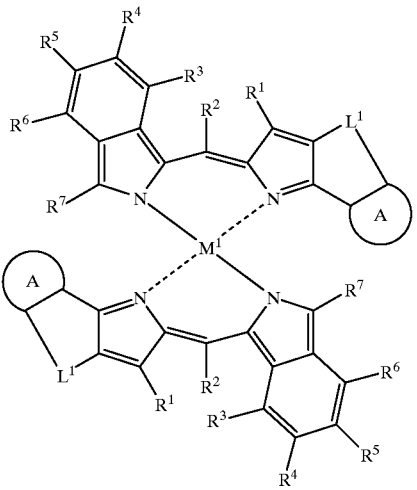

wherein $R^1$ to $R^6$ independently represent hydrogen, halogen, nitro, cyano, hydroxyl, amino, carboxyl, sulfo, substituted or unsubstituted alkyl with up to 20 carbon atoms, alkoxy, alkylthio, aryloxy, arylthio, alkenyl, acyl, alkoxycarbonyl, carbamoyl, acylamino, aralkyl, aryl or heteroaryl; $R^7$ represents halogen, aryl, heteroaryl, alkoxy, alkylthio, aryloxy or arylthio; A represents substituted or unsubstituted aromatic or heterocyclic ring with up to 20 carbon atoms; $L^1$ represents substituted or unsubstituted bivalent residue forming a ring together with carbon atoms to which it attaches and optionally containing a hetero atom; and $M^1$ represents transition metal element.

33 Claims, 1 Drawing Sheet

DIPYRROMETHENE-METAL CHELATE COMPOUND AND OPTICAL RECORDING MEDIUM USING THEREOF

BACKGROUND OF THE INVENTION

1. Field of the Invention

This invention relates to a novel dipyrromethene-metal chelate compound, and an optical recording medium using thereof which can perform recording and regenerating with a higher density than that of the prior art.

2. Description of the Related Art

To date, a DVD with a capacity of 4.7 GB has been developed and marketed as an optical recording medium with a larger capacity than a CD. Since the DVD is a read-only medium, there has been needed an optical recording medium capable of recording and regenerating comparable to the capacity. Among others, a rewritable type is called a DVD-R.

In a DVD for high-density recording, an oscillation wavelength of a laser is 630 nm to 680 nm which is shorter than that for a CD. As dyes for an organic-dye optical recording medium for such a shorter wavelength, cyanine, azo, bezopyran, benzodifuranone, indigo, dioxadine, porphyrin dyes, etc. have been suggested in, for example, JP-A 4-74690, JP-A 5-38878, JP-A 6-40161, JP-A 6-40162, JP-A 6-199045, JP-A 6-336086, JP-A 7-76169, JP-A 7-125441, JP-A 7-262604, JP-A 9-156218, JP-A 9-193544, JP-A 9-193545, JP-A 9-193547, JP-A 9-194748, JP-A 9-202052, JP-A 9-267562 and JP-A 9-274732. There have been, however, solved various problems such as poor durability, those inherent to use of a short wavelength including a poor jitter due to a larger distributed pit formation caused by much influence on the surrounding area whereas a small pit must be formed with a focus laser beam, deteriorated crosstalk in a radius direction, a poor modulation degree due to an extremely small pit or reduction in a reflectance or sensitivity caused by selecting an organic dye having an inappropriate optical constant such as a refractive index and an extinction coefficient for a desired laser wavelength in a recording layer.

Furthermore, as in increase of a recording speed in a CD-R, there has been desired to provide an optical recording medium which can deal with recording at double speed or more compared with usual recording speed for a DVD-R. However, there remain the problems such as poor recording sensitivity associated with high-speed recording and a poor jitter.

We have already suggested an optical recording medium using a dipyrromethene-metal chelate compound in, for example, JP-A10-226172, JP-A11-092682, JP-A11-165465, JP-A11-227332, JP-A11-227333 and JP-A11-321098. However, there has not been solved a problem of deterioration in recording properties associated with the above high-speed recording, and thus, further improvement has been needed.

SUMMARY OF THE INVENTION

Thus, an objective of this invention is to provide a highly durable optical recording medium capable of recording and regenerating with a short wavelength of laser with a wavelength of 520 to 690 nm and suitable to high-density and high-speed recording.

We have intensely investigated an optical recording medium using a dipyrromethene-metal chelate compound disclosed in, for example, JP-A 10-226172 above and have finally found that for a dipyrromethene-metal chelate compounds, a particular substituent may be selected to provide an optical recording medium which is excellent in recording properties and durability as well as can deal with recording at a higher speed than a recording speed in the prior art, to achieve this invention. Thus, this invention relates to:

[1] An optical recording medium comprising at least a recording layer and a reflecting layer on a substrate wherein the recording layer contains at least one dipyrromethene-metal chelate compound represented by general formula (1):

(1)

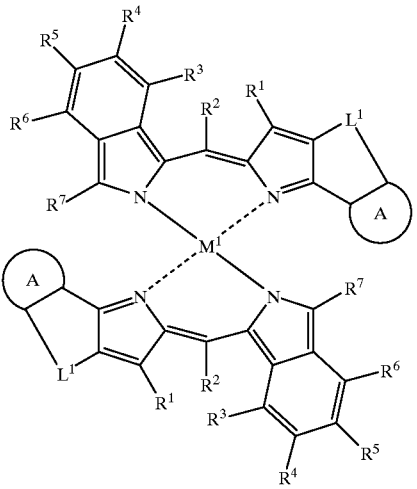

wherein $R^1$ to $R^6$ independently represent hydrogen, halogen, nitro, cyano, hydroxyl, amino, carboxyl, sulfo, substituted or unsubstituted alkyl with up to 20 carbon atoms, alkoxy, alkylthio, aryloxy, arylthio, alkenyl, acyl, alkoxycarbonyl, carbamoyl, acylamino, aralkyl, aryl or heteroaryl; $R^7$ represents halogen, aryl, heteroaryl, alkoxy, alkylthio, aryloxy or arylthio; A represents substituted or unsubstituted aromatic or heterocyclic ring with up to 20 carbon atoms; $L^1$ represents substituted or unsubstituted bivalent residue forming a ring together with carbon atoms to which it attaches and optionally containing a hetero atom; and $M^1$ represents transition metal element;

[2] The optical recording medium as described in [1] wherein the dipyrromethene-metal chelate compound is a dipyrromethene-metal chelate compound represented by general formula (2):

(2)

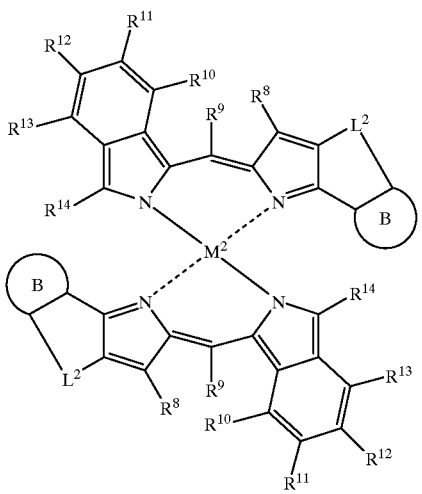

wherein $R^8$ to $R^{13}$ independently represent hydrogen, halogen, nitro, cyano, hydroxyl, amino, carboxyl, sulfo, substituted or unsubstituted alkyl with up to 20 carbon atoms, alkoxy, alkylthio, aryloxy, arylthio, alkenyl, acyl, alkoxycarbonyl, carbamoyl, acylamino, aralkyl, aryl or heteroaryl; $R^{14}$ represents halogen, aryl, heteroaryl, alkoxy, alkylthio, aryloxy or arylthio; B represents substituted or unsubstituted aromatic or heterocyclic ring with up to 20 carbon atoms; $L^2$ represents substituted or unsubstituted alkylene residue forming a ring together with carbon atoms to which it attaches; and $M^2$ represents transition metal element;

[3] The optical recording medium as described in [2] wherein the dipyrromethene-metal chelate compound is a dipyrromethene-metal chelate compound represented by general formula (3):

(3)

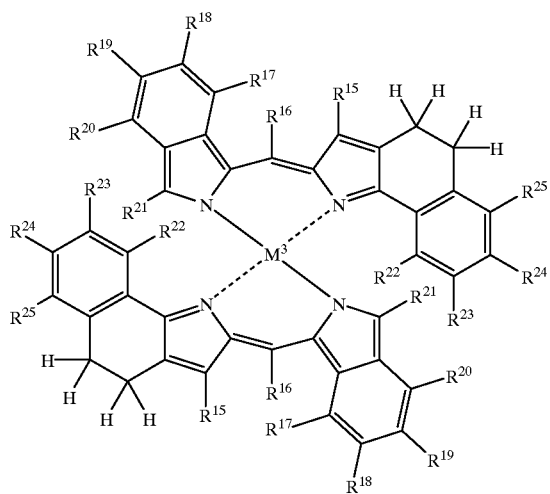

wherein $R^{15}$ to $R^{20}$, $R^{22}$ to $R^{25}$ independently represent hydrogen, halogen, nitro, cyano, hydroxyl, amino, carboxyl, sulfo, substituted or unsubstituted alkyl with up to 20 carbon atoms, alkoxy, alkylthio, aryloxy, arylthio, alkenyl, acyl, alkoxycarbonyl, carbamoyl, acylamino, aralkyl, aryl or heteroaryl; $R^{21}$ represents halogen, substituted or unsubstituted aryl with up to 20 carbon atoms, heteroaryl, alkoxy, alkylthio, aryloxy or arylthio; $M^3$ represents transition metal element;

[4] The optical recording medium as described in [1] wherein $R^1$ in general formula (1) is halogen;

[5] The optical recording medium as described in [2] wherein $R^8$ in general formula (2) is halogen;

[6] The optical recording medium as described in [3] wherein $R^{15}$ in general formula (3) is halogen;

[7] The optical recording medium as described in any of [1] to [6] wherein the recording layer further contains at least one dipyrromethene-metal chelate compound represented by general formula (4):

(4)

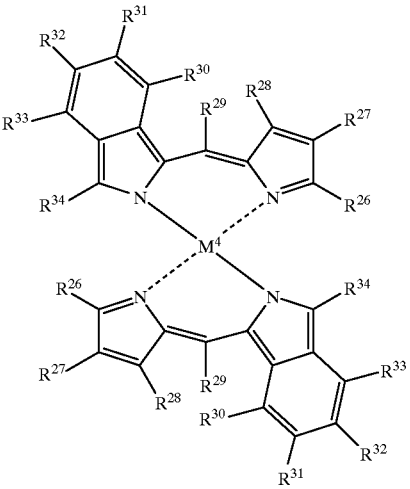

wherein $R^{26}$ to $R^{33}$ independently represent hydrogen, halogen, nitro, cyano, hydroxyl, amino, carboxyl, sulfo, substituted or unsubstituted alkyl with up to 20 carbon atoms, alkoxy, alkylthio, aryloxy, arylthio, alkenyl, acyl, alkoxycarbonyl, carbamoyl, acylamino, aralkyl, aryl or heteroaryl; $R^{34}$ represents halogen, substituted or unsubstituted aryl with up to 20 carbon atoms, heteroaryl, alkoxy, alkylthio, aryloxy or arylthio; and $M^4$ represents transition metal element;

[8] The optical recording medium as described in any of [1] to [7] wherein the recording layer has a refractive index of at least 1.8 at a laser wavelength and an extinction coefficient of 0.04 to 0.40;

[9] The optical recording medium as described in any of [1] to [7] wherein recording and regenerating can be performed for a laser beam with a wavelength within a range of 520 to 690.

This invention also relates to a dipyrromethene-metal chelate compound defined in any of the above [1] to [6].

A dipyrromethene-metal chelate compound can be used as a recording layer to provide a highly-durable rewritable optical recording medium capable of recording and regenerating using a laser with a wavelength of 520 to 690 nm and suitable to high-density and high-speed recording which is considerably expected to be as a high-density recording medium.

DETAILED DESCRIPTION OF THE PREFERRED EMBODIMENTS

Figure 1:
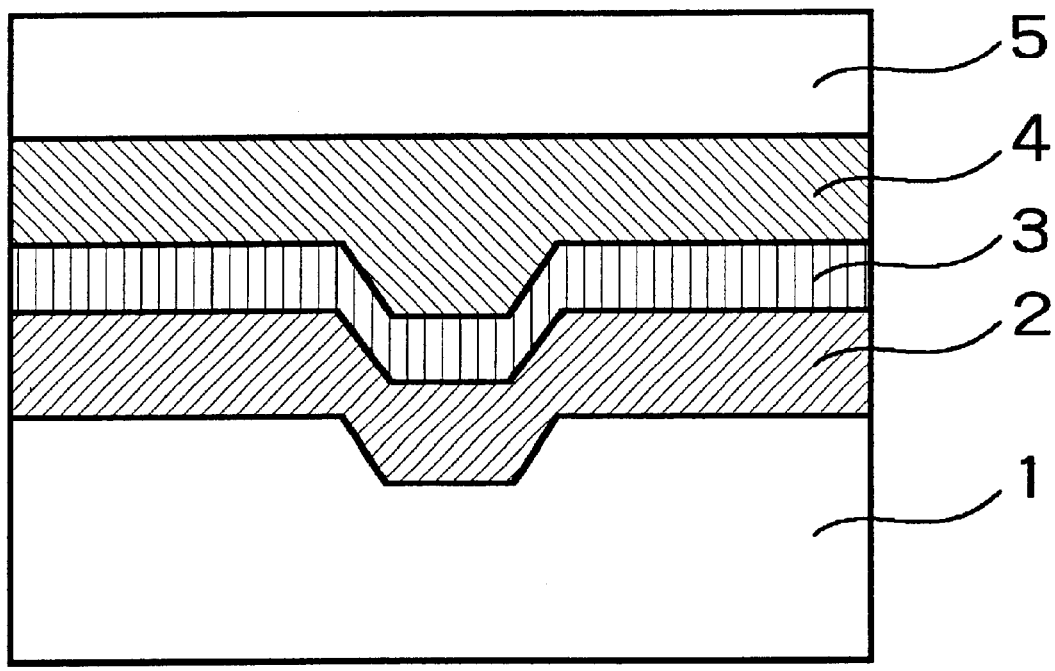
FIG. 1 is a cross-sectional structural drawing illustrating layer structures in optical recording media according to the prior art and this invention.

This invention will be described in detail.

There will be described a dipyrromethene-metal chelate compound represented by general formula (1).

Examples of $R^1$ to $R^6$ include hydrogen; halogens such as fluorine, chlorine, bromine and iodine; nitro; cyano; hydroxyl; amino; carboxyl; sulfo; substituted or unsubstituted alkyls with up to 20 carbon atoms such as methyl, ethyl, n-propyl, isopropyl, n-butyl, isobutyl, sec-butyl, t-butyl, n-pentyl, isopentyl, 2-methylbutyl, 1-methylbutyl, neopentyl, 1,2-dimethylpropyl, 1,1-dimethylpropyl, cyclopentyl, n-hexyl, 4-methylpentyl, 3-methylpentyl, 2-methylpentyl, 1-methylpentyl, 3,3-dimethylbutyl, 2,3-dimethylbutyl, 1,3-dimethylbutyl, 2,2-dimethylbutyl, 1,2-dimethylbutyl, 1,1-dimethylbutyl, 3-ethylbutyl, 2-ethylbutyl, 1-ethylbutyl, 1,2,2-trimethylbutyl, 1,1,2-trimethylbutyl, 1-ethyl-2-methylpropyl, cyclohexyl, n-heptyl, 2-methylhexyl, 3-methylhexyl, 4-methylhexyl, 5-methylhexyl, 2,4-dimethylpentyl, n-octyl, 2-ethylhexyl, 2,5-dimethyhexyl, 2,5,5-trimethylpentyl, 2,4-dimethylhexyl, 2,2,4-trimethylpentyl, 3,5,5-trimethylhexyl, n-nonyl, n-decyl, 4-ethyloctyl, 4-ethyl-4,5-dimethylhexyl, n-undecyl, n-dodecyl, 1,3,5,7-tetraethyloctyl, 4-butyloctyl, 6,6-diethyloctyl, n-tridecyl, 6-methyl-4-butyloctyl, n-tetradecyl, n-pentadecyl, 3,5-dimethylheptyl, 2,6-dimethylheptyl, 2,4-dimethylheptyl, 2,2,5,5-tetramethylhexyl, 1-cyclopentyl-2,2-dimethylpropyl and 1-cyclohexyl-2,2-dimethylpropyl; alkoxys such as methoxy, ethoxy, n-propoxy, isopropoxy, n-butoxy, isobutoxy, sec-butoxy, t-butoxy, n-pentoxy, isopentoxy, neopentoxy, n-hexyloxy and n-dodecyloxy; alkylthios such as methylthio, ethylthio, n-propylthio, isopropylthio, n-butylthio, isobutylthio, sec-butylthio, t-butylthio, n-pentylthio, isopentylthio, 2-methylbutylthio, 1-methylbutylthio, neopentylthio, 1,2-dimethylpropylthio and 1,1-dimethylpropylthio; aryloxys such as phenoxy, 2-methylphenoxy, 4-methylphenoxy, 4-t-butylphenoxy, 2-methoxyphenoxy and 5-isopropylphenoxy; arylthios such as phenylthio, 4-methylphenylthio, 2-methoxyphenylthio and 4-t-butylphenylthio; alkenyls such as vinyl, propenyl, 1-butenyl, isobutenyl, 1-pentenyl, 2-pentenyl, 2-methyl-1-butenyl, 3-methyl-1-butenyl, 2-methyl-2-butenyl, 2,2-dicyanovinyl, 2-cyano-2-methylcarboxylvinyl, 2-cyano-2-methylsulfonevinyl and 2-phenyl-1-butenyl; acyls such as formyl, acetyl, ethylcarbonyl, n-propylcarbonyl, isopropylcarbonyl, n-butylcarbonyl, isobutylcarbonyl, sec-butylcarbonyl, t-butylcarbonyl, n-pentylcarbonyl, isopentylcarbonyl, neopentylcarbonyl, 2-methylbutylcarbonyl and nitrobenzylcarbonyl; alkoxycarbonyls such as methoxycarbonyl, ethoxycarbonyl, isopropyloxycarbonyl and 2,4-dimethylbutyloxycarbonyl; carbamoyl; acylaminos such as acetylamino, ethylcarbonylamino and butylcarbonylamino; aralkyls such as benzyl, nitrobenzyl, cyanobenzyl, hydroxybenzyl, methylbenzyl, dimethylbenzyl, trimethylbenzyl, dichlorobenzyl, methoxybenzyl, ethoxybenzyl, trifluoromethylbenzyl, naphthylmethyl, nitronaphthylmethyl, cyanonaphthylmethyl, hydroxynaphthylmethyl, methylnaphthylmethyl and trifluoromethylnaphthylmethyl; aryls such as phenyl, nitrophenyl, cyanophenyl, hydroxyphenyl, methylphenyl, dimethylphenyl, trimethylphenyl, ethylphenyl, diethylphenyl, triethylphenyl, n-propylphenyl, di(n-propyl)phenyl, tri(n-propyl)phenyl, isopropylphenyl, di(isopropyl)phenyl, tri(isopropyl)phenyl, n-butylphenyl, di(n-butyl)phenyl, tri(n-butyl)phenyl, isobutylphenyl, di(isobutyl)phenyl, tri(isobutyl)phenyl, sec-butylphenyl, di(sec-butyl)phenyl, tri(sec-butyl)phenyl, t-butylphenyl, di(t-butyl)phenyl, tri(t-butyl)phenyl, dimethyl-t-butylphenyl, fluorophenyl, chlorophenyl, bromophenyl, iodophenyl, methoxyphenyl, ethoxyphenyl, trifluoromethylphenyl, N,N-dimethylaminophenyl, naphthyl, nitronaphthyl, cyanonaphthyl, hydroxynaphthyl, methylnaphthyl, fluoronaphthyl, chloronaphthyl, bromonaphthyl, iodonaphthyl, methoxynaphthyl, trifluoromethylnaphthyl and N,N-dimethylaminonaphthyl; heteroaryls such as pyrrolyl, thienyl, furanyl, oxazoyl, isoxazoyl, oxadiazoyl, imidazoyl, benzoxazoyl, benzothiazoyl, benzimidazoyl, benzofuranyl, indolyl and isoindolyl.

Examples of $R^7$ include halogens such as fluorine, chlorine, bromine and iodine; aryls such as phenyl, nitrophenyl, cyanophenyl, hydroxyphenyl, methylphenyl, dimethylphenyl, trimethylphenyl, ethylphenyl, diethylphenyl, triethylphenyl, n-propylphenyl, di(n-propyl)phenyl, tri(n-propyl)phenyl, isopropylphenyl, di(isopropyl)phenyl, tri(isopropyl)phenyl, n-butylphenyl, di(n-butyl)phenyl, tri(n-butyl)phenyl, isobutylphenyl, di(isobutyl)phenyl, tri(isobutyl)phenyl, sec-butylphenyl, di(sec-butyl)phenyl, tri(sec-butyl)phenyl, t-butylphenyl, di(t-butyl)phenyl, tri(t-butyl)phenyl, dimethyl-t-butylphenyl, fluorophenyl, chlorophenyl, bromophenyl, iodophenyl, methoxyphenyl, ethoxyphenyl, trifluoromethylphenyl, N,N-dimethylaminophenyl, naphthyl, nitronaphthyl, cyanonaphthyl, hydroxynaphthyl, methylnaphthyl, fluoronaphthyl, chloronaphthyl, bromonaphthyl, iodonaphthyl, methoxynaphthyl, trifluoromethylnaphthyl and N,N-dimethylaminonaphthyl; heteroaryls such as pyrrolyl, thienyl, furanyl, oxazoyl, isoxazoyl, oxadiazoyl, imidazoyl, benzoxazoyl, benzothiazoyl, benzimidazoyl, benzofuranyl, indolyl and isoindolyl; alkoxys such as methoxy, ethoxy, n-propoxy, isopropoxy, n-butoxy, isobutoxy, sec-butoxy, t-butoxy, n-pentoxy, isopentoxy, neopentoxy, n-hexyloxy and n-dodecyloxy; alkylthios such as methylthio, ethylthio, n-propylthio, isopropylthio, n-butylthio, isobutylthio, sec-butylthio, t-butylthio, n-pentylthio, isopentylthio, 2-methylbutylthio, 1-methylbutylthio, neopentylthio, 1,2-dimethylpropylthio and 1,1-dimethylpropylthio; aryloxys such as phenoxy, 2-methylphenoxy, 4-methylphenoxy, 4-t-butylphenoxy, 2-methoxyphenoxy and 4-isopropylphenoxy; arylthios such as phenylthio, 4-methylphenylthio, 2-methoxyphenylthio and 4-t-butylphenylthio.

Example of A include aromatics such as benzene, nitrobenzene, cyanobenzene, hydroxybenzene, methylbenzene, dimethylbenzene, trimethylbenzene, ethylbenzene, diethylbenzene, triethylbenzene, n-propylbenzene, di(n-propyl)benzene, tri(n-propyl)benzene, isopropylbenzene, di(isopropyl)benzene, tri(isopropyl)benzene, n-butylbenzene, di(n-butyl)benzene, tri(n-butyl)benzene, isobutylbenzene, di(isobutyl)benzene, tri(isobutyl)benzene, sec-butylbenzene, di(sec-butyl)benzene, tri(sec-butyl)benzene, t-butylbenzene, di(t-butyl)benzene, tri(t-butyl)benzene, dimethyl-t-butylbenzene, phenylbenzene, carboxybenzene, fluorobenzene, chlorobenzene, bromobenzene, iodobenzene, methoxybenzene, ethoxybenzene, trifluoromethylbenzene, N,N-dimethylaminobenzene, naphthalene, nitronaphthalene, cyanonaphthalene, hydroxynaphthalene, methylnaphthalene, fluoronaphthalene, chloronaphthalene, bromonaphthalene, iodonaphthalene, methoxynaphthalene, trifluoromethylnaphthalene and N,N-dimethylaminonaphthalene; and heterocycles such as pyrrole, N-methylpyrrole, thiophene, methylthiophene, furan, oxazole, isoxazole, oxadiazole, imidazole, benzoxazole, benzothiazole, benzimidazole, benzofuran, indole and isoindole.

$L^1$ represents substituted or unsubstituted bivalent residue optionally containing a hetero atom and forms a ring together with carbon atoms to which it attaches. Examples of a ring formed by $L^1$ with carbon atoms to which it attaches include substituted or unsubstituted five-, six- and seven-membered rings, preferably substituted or unsubstituted five- and six-membered rings, more preferably substituted or unsubstituted six-membered ring.

Examples of $L^1$ forming a five-membered ring include —$CH_2$—, —CH(F)—, —CH(Cl)—, —CH(Br)—, —CH(I)—, —$C(F)_2$—, —$C(Cl)_2$—, —$C(Br)_2$—, —$C(I)_2$—, —$CH(CH_3)$—, —$C(CH_3)_2$—, —$CH(OCH_3)$—, —$C(OCH_3)_2$—, —O— and —S—.

Examples of $L^1$ forming a six-membered ring include —$CH_2CH_2$—, —$CH(F)CH_2$—, —$CH(Cl)CH_2$—, —CH(Br)$CH_2$—, —$CH(I)CH_2$—, —$C(F)_2CH_2$—, —$C(Cl)_2CH_2$—, —$C(Br)_2CH_2$—, —$C(I)_2CH_2$—, —$C(F)_2C(F)_2$—, —$C(Cl)_2C(Cl)_2$—, —$C(Br)_2C(Br)_2$—, —$C(I)_2C(I)_2$—, —$CH(CH_3)CH_2$—, —$CH(CH_3)CH(CH_3)$—, —$C(CH_3)_2CH_2$—, —$C(CH_3)_2C(CH_3)_2$—, —CH ($OCH_3)CH_2$—, —$CH(OCH_3)CH(OCH_3)$—, —$C(OCH_3)_2CH_2$— and —$C(OCH_3)_2C(OCH_3)_2$—.

Examples of $L^1$ forming a seven-membered ring include —$CH_2CH_2CH_2$—, —$CH_2CH(F)CH_2$—, —$CH_2CH(Cl)CH_2$—, —$CH_2CH(Br)$ $CH_2$—, —$CH_2CH(I)CH_2$—, —$CH_2C(F)_2CH_2$—, —$CH_2C(Cl)_2CH_2$—, —$CH_2C(Br)_2CH_2$—, —$CH_2C(I)_2CH_2$—, —$CH_2CH(CH_3)CH_2$—, —$CH_2C(CH_3)_2CH_2$—, —$CH_2CH(OCH_3)CH_2$—, —$CH_2C(OCH_3)_2CH_2$—, —$CH_2OCH_2$— and —$CH_2SCH_2$—.

There are no restrictions for $M^1$ as long as it is a transition metal element capable of forming a chelate with a dipyrromethene compound; for example, Groups 8, 9, 10 (Group VIII), Group 11 (Group Ib), Group 12 (Group IIb), Group 3 (Group IIIa), Group 4 (Group IVa), Group 5 (Group Va), Group 6 (Group VIa) and Group 7 (Group VIIa) metals, preferably nickel, cobalt, iron, ruthenium, rhodium, palladium, copper, osmium, iridium, platinum and zinc, particularly copper and cobalt in the light of light resistance.

The dipyrromethene-metal chelate compound represented by general formula (2) is a preferable subgroup of general formula (1), and examples of $R^8$ to $R^{13}$ are as defined for $R^1$ to $R^6$ in general formula (1), including hydrogen; halogens such as fluorine, chlorine, bromine and iodine; nitro; cyano; hydroxyl; amino; carboxyl; sulfo; the above substituted or unsubstituted alkyls with up to 20 carbon atoms; the above alkoxys; the above alkylthios; the above aryloxys; the above arylthios; the above alkenyls; the above acyls; the above alkoxycarbonyls; carbamoyl; the above acylaminos; the above aralkyls; the above aryls; and the above heteroaryls. In the light of recording sensitivity and high-speed recording properties, preferable examples of $R^8$ include the above halogens.

Examples of $R^{14}$ are as defined for $R^7$ in general formula (1), including the above halogens; the above aryls; the above heteroaryls; the above alkoxys; the above alkylthios; the above aryloxys; and the above arylthios.

Examples of B areas defined for the above A, and examples of $L^2$ include, among those for the above $L^1$, substituted or unsubstituted alkylene residues with no hetero atoms, particularly alkyl substituted or unsubstituted alkylene residues.

$M^2$ may be any transition metal element as long as it can form a chelate with a dipyrromethene compound, specifically including metals of Groups 8, 9, 10 (Group VIII), Group 11 (Group Ib), Group 12 (Group IIb), Group 3 (Group IIIa), Group 4 (Group IVa), Group 5 (Group Va), Group 6 (Group VIa) and Group 7 (Group VIIa), preferably nickel, cobalt, iron, ruthenium, rhodium, palladium, copper, osmium, iridium, platinum and zinc. In the light of light resistance, copper and cobalt are particularly preferable.

A dipyrromethene-metal chelate compound represented by general formula (3) is a more preferable subgroup of general formula (1). In general formula (3), examples of $R^{15}$ to $R^{20}$, $R^{22}$ to $R^{25}$ are as defined for $R^1$ to $R^6$ in general formula (1), including hydrogen; halogens such as fluorine, chlorine, bromine and iodine; nitro; cyano; hydroxyl; amino; carboxyl; sulfo; the above substituted or unsubstituted alkyls with up to 20 carbon atoms; the above alkoxys; the above alkylthios; the above aryloxys; the above arylthios; the above alkenyls; the above acyls; the above alkoxycarbonyls; carbamoyl; the above acylaminos; the above aralkyls; the above aryls; and the above heteroaryls. In particular, the above halogens are preferable as examples of $R^{15}$ in the light of recording sensitivity and high-speed recording properties.

Examples of $R^{21}$ are as defined for $R^7$ in general formula (1), including the above halogens; the above aryls; the above heteroaryls; the above alkoxys; the above alkylthios; the above aryloxys; and the above arylthios.

Examples of $M^3$ may be any transition metal element as long as it can form a chelate with a dipyrromethene compound, including the metals of Groups 8, 9, 10 (Group VIII), Group 11 (Group Ib, Group 12 (Group IIb), Group 3 (Group IIIa), Group 4 (Group IVa), Group 5 (Group Va), Group 6 (Group VIa) and Group 7 (Group VIIa), preferably nickel, cobalt, iron, ruthenium, rhodium, palladium, copper, osmium, iridium, platinum and zinc. In the light of light resistance, copper and cobalt are particularly preferable.

A dipyrromethene-metal chelate compound of this invention represented by general formula (1) may be, for example, prepared as described in, but not limited to, Aust. J. Chem, 1965, 11, 1835–45, Heteroatom Chemistry, Vol. 1, 5,389 (1990), U.S. Pat. No. 4,774,339 or U.S. Pat. No. 5,433,896. It may be typically prepared by the following two-step reaction.

In the first step, a compound represented by general formula (5) is reacted with a compound represented by general formula (6) or a compound represented by general formula (7) is reacted with a compound represented by general formula (8) in the presence of an acid catalyst such as hydrobromic acid and hydrochloric acid in an appropriate solvent, to give a dipyrromethene compound represented by general formula (9). Then, in the second step, the dipyrromethene compound represented by general formula (9) is reacted with an acetate or halide of a metal such as nickel, cobalt, iron, ruthenium, rhodium, palladium, copper, osmium, iridium, platinum and zinc, to give the dipyrromethene-metal chelate compound represented by general formula (1):

wherein in formulas (5) to (9), $L^1$, $R^1 \sim R^7$ and A are as defined for the above $L^1$, $R^1 \sim R^7$ and A, respectively.

A compound represented by formula (6) or (8) as a material introducing a characteristic structure in the compound of this invention may be prepared according to the following reaction.

The compound represented by general formula (6) may be, for example, prepared as described in, but not limited to, Zhurnal Organicheskoj Khimii, 492–495(1984), Liebigs Ann. Chem. 3847–3853(1965), Chem. Ber. 110, 491–499 (1977). Typically, the compound represented by general formula (6) may be prepared by preparing a ketoxime derivative from a compound represented by general formula (10) and reacting it with dichloroethane in the presence of a base catalyst such as potassium hydroxide in a solvent such as dimethylsulfoxide, or alternatively by reacting the compound represented by general formula (10) with 1-nitro-2-dimethylaminoethylene or glyoxal-mono (dimethylhydrazone) in the presence of an alkoxide in an appropriate solvent to give a 2-nitroethylidene-tetrarone derivative or 2-(dimethylhydrazone)ethylidene-tetrarone derivative and then reducing the product with, for example, hydrosulfite.

The compound represented by general formula (8) may be prepared by acylating the compound represented by general formula (6), for example, according to, but not limited to, a method described in Organic Preparations and Procedures Int. 13(2), 97–101(1981), J.O.C. 28, 3052–3058(1963) or Tetrahedron Letters 2411- (1989):

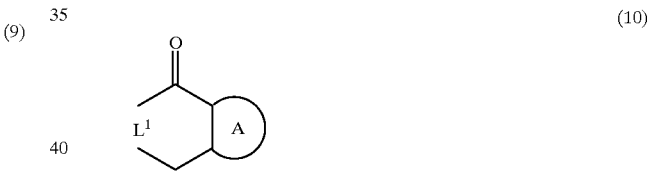

wherein $L^1$ and A are as defined above.

Table 1 shows examples of a dipyrromethene-metal chelate compound represented by general formula (1).

TABLE 1
| Comp. | L¹ | R¹ | R² | R³ | R⁴ | R⁵ | R⁶ | R⁷ | A | M¹ |
|---|---|---|---|---|---|---|---|---|---|---|
| 1-1 | —CH₂—CH₂— | H | H | H | H | Br | H | 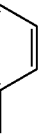 | 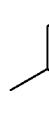 | Cu |
| 1-2 | —CH₂—CH₂— | H | H | H | H | H | H | 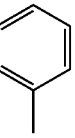 | 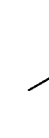 | Cu |
| 1-3 | —CH₂—CH₂— | H | CH₃ | H | H | Br | H | 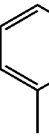 | 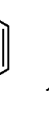 | Cu |
| 1-4 | —CH₂—CH₂— | H | H | H | H | Cl | H | (i-Pr, i-Pr substituted phenyl) | (o-tolyl) | Cu |
| 1-5 | —CH₂—CH₂— | H | H | H | Cl | Cl | H | (i-Pr, i-Pr substituted phenyl) | (o-tolyl) | Cu |
| 1-6 | —CH₂—CH₂— | H | H | H | H | Br | H | (Me, Me substituted phenyl) | (o-tolyl) | Cu |

TABLE 1-continued

| Comp. | L¹ | R¹ | R² | R³ | R⁴ | R⁵ | R⁶ | R⁷ | A | M¹ |
|---|---|---|---|---|---|---|---|---|---|---|
| 1-7 | —CH₂—CH₂— | Br | H | H | H | H | H | phenyl (Me) | 2,3-dimethyl-6-MeO-phenyl | Cu |
| 1-8 | —CH₂—CH₂— | H | CH₃ | H | H | H | H | Br | 3,4-dimethyl-5-Br-phenyl | Cu |
| 1-9 | —CH₂—CH₂— | H | CH₃ | Cl | Cl | Cl | Cl | —S-t-Bu | 2,3-dimethylphenyl | Mn |
| 1-10 | —CH₂—CH₂— | H | H | H | Br | H | H | 2,4-di-i-Pr-phenyl | 3,4-dimethyl-6-OMe-phenyl | Ni |
| 1-11 | —CH₂—CH₂— | H | C₂H₅ | H | H | H | H | 3,4,5-Me,t-Bu,Me-phenyl | 2,3-dimethyl-6-NO₂-phenyl | Cu |
| 1-12 | —CH₂—CH₂— | NO₂ | H | H | H | Cl | H | 4-NMe₂-phenyl (Me) | 2-methylphenyl | Co |

TABLE 1-continued

| Comp. | L¹ | R¹ | R² | R³ | R⁴ | R⁵ | R⁶ | R⁷ | A | M¹ |
|---|---|---|---|---|---|---|---|---|---|---|
| 1-13 | —CH₂—CH₂— | CN | H | Cl | Cl | Cl | Cl | 4-Me-phenyl | 2-Me-phenyl | Zn |
| 1-14 | —CH₂—CH₂— | OCH₃ | H | H | H | OCH₃ | H | 4-OMe-phenyl | 2-Me-phenyl | Zn |
| 1-15 | —CH₂—CH₂— | H | CH₃ | H | H | H | H | 2,5-dimethyl-4-methyl-1H-pyrrol-3-yl | 3-Me-4-OMe-phenyl | Ni |
| 1-16 | —CH₂—CH₂— | COCH₃ | H | H | H | Cl | H | Cl | 2-Me-phenyl | Cu |
| 1-17 | —CH₂—CH₂— | CO₂CH₃ | phenyl | CH₃ | H | H | CH₃ | 3-Et-2,4,5-trimethyl-1H-pyrrol-... | 2-Me-phenyl | Cu |
| 1-18 | —CH₂—CH₂— | H | 2,6-dimethyl-... mesityl | H | H | H | H | phenyl | 3,5-dimethylphenyl | Cu |
| 1-19 | —CH₂—CH₂— | SO₃H | H | H | H | Br | H | 4-Et-phenyl | 2-Me-phenyl | Ni |

TABLE 1-continued
| Comp. | L¹ | R¹ | R² | R³ | R⁴ | R⁵ | R⁶ | R⁷ | A | M¹ |
|---|---|---|---|---|---|---|---|---|---|---|
| 1-20 | —CH₂—CH₂— | NHCOCH₃ | H | H | H | Br | H | —S-t-Bu |  | Cu |
| 1-21 | —CH₂—CH₂— | H | CN | H | H | H | H |  | 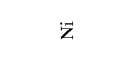 | Zn |
| 1-22 | —CH₂—CH₂— | H | C₂H₅ | H | H | H | H | Br |  | Fe |
| 1-23 | —CH₂—CH₂— | 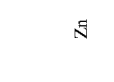 | H | H | H | —CH=CHCH₃ | H |  |  | Co |
| 1-24 | —CH₂—CH₂— | H | H | H | H | H | H | |  | Mn |
| 1-25 | —CH₂—CH₂— | H | CH₃ | CH₃ | H | H | CH₃ | | 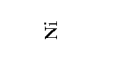 | Zn |
| 1-26 | —CH₂—CH₂— | OH | H | H | H | H | H | |  | Ni |

TABLE 1-continued

| Comp. | L¹ | R¹ | R² | R³ | R⁴ | R⁵ | R⁶ | R⁷ | A | M¹ |
|---|---|---|---|---|---|---|---|---|---|---|
| 1-27 | —CH₂—CH₂— | H | H | H | Br | H | H | 2,4,6-trimethylphenyl | 2-methylphenyl | Co |
| 1-28 | —CH₂—CH₂— | Br | H | H | O-n-Bu | H | H | phenyl | 2-methylphenyl | Co |
| 1-29 | —CH₂—CH₂— | CH₃ | CN | H | H | H | H | Cl | 4-carboxy-3-methylphenyl | Cu |
| 1-30 | —CH₂—CH₂— | H | CH₃ | H | —S—phenyl | H | H | 4-(NEt₂)-phenyl (with methyl) | 2,3,4,5,6-pentabromo-methylphenyl | Cu |
| 1-31 | —CH₂—CH₂— | H | 1-methyl-pyrrol-2-yl / phenyl | H | H | H | H | OC₂H₅ | 2-methylphenyl | Ni |
| 1-32 | —CH₂—CH₂— | H | H | H | Cl | H | H | 2,4,6-trimethylphenyl | 2-methylphenyl | Mn |

TABLE 1-continued
| Comp. | $L^1$ | $R^1$ | $R^2$ | $R^3$ | $R^4$ | $R^5$ | $R^6$ | $R^7$ | A | $M^1$ |
|---|---|---|---|---|---|---|---|---|---|---|
| 1-33 | —$CH_2$—$CH_2$— | $CONH_2$ | H | H | Br | H | H | 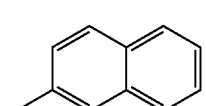 | 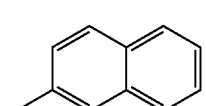 | Zn |
| 1-34 | —$CH_2$—$CH_2$— | $NH_2$ | H | H | Br | H | H | Cl | 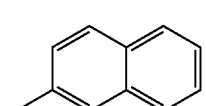 | Cu |
| 1-35 | —$CH_2$—$CH_2$— | $CO_2H$ | H | H | H | Br | H | 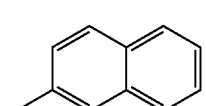 | 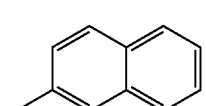 | Cu |
| 1-36 | —$CH_2$—$CH_2$— | 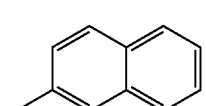 | $CH_3$ | H | H | Br | H |  |  | Fe |
| 1-37 | —$CH_2$—$CH_2$— |  | $CH_3$ | H | H | Cl | H |  |  | Cu |
| 1-38 | —$CH_2$—$CH_2$— | $SCH_3$ | H | H | H | Br | H |  |  | Zn |

TABLE 1-continued

| Comp. | L¹ | R¹ | R² | R³ | R⁴ | R⁵ | R⁶ | R⁷ | A | M¹ |
|---|---|---|---|---|---|---|---|---|---|---|
| 1-39 | —CH₂—CH₂— | H | H | H | H | H | H | 2,4-dimethylphenyl | 3,4-dimethylbiphenyl | Zn |
| 1-40 | —CH₂—CH₂— | H | CH₃ | H | H | H | H | n-Hex (4-Br-2-Me-phenyl-NH-) | 2,3-dimethylnaphthalene | Co |
| 1-41 | —CH₂—CH₂— | H | C₂H₅ | H | H | H | H | Cl | 1,2-dimethylnaphthalene | Cu |
| 1-42 | —CH₂—CH₂— | H | H | Br | H | Br | H | H | 3,4-dimethyl-benzoic acid (CO₂H) | Mn |
| 1-43 | —CH₂—CH₂— | Br | H | H | H | H | H | 2,4-dimethylphenyl (Me) | 2,3-dimethylphenyl | Ni |
| 1-44 | —CH₂—CH₂— | H | CH₃ (phenoxy, —O-phenyl) | H | H | Cl | H | OC₂H₅ | 2,3-dimethylphenyl | Mn |
| 1-45 | —CH₂—CH₂— | —CH=CHCH₃ | H | H | H | H | H | 2,4-di-i-Pr-phenyl (with Me) / phenoxy (—OMe) | 2,3-dimethylphenyl | Cu |

TABLE 1-continued
| Comp. | L¹ | R¹ | R² | R³ | R⁴ | R⁵ | R⁶ | R⁷ | A | M¹ |
|---|---|---|---|---|---|---|---|---|---|---|
| 1-46 | —CH₂—CH₂— | Br | H | H | Br | H | H | 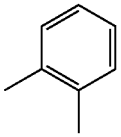 | 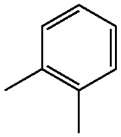 | Cu |
| 1-47 | —CH₂—CH₂— | Br | H | H | H | Br | H | 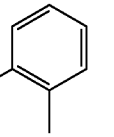 | 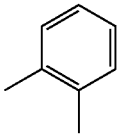 | Cu |
| 1-48 | —CH₂—CH₂— | Br | H | H | H | CH₃ | H | 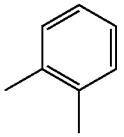 | 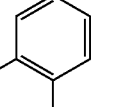 | Cu |
| 1-49 | —CH₂—CH₂— | Br | H | H | H | OCH₃ | H | Me-Me-Me (Me) | o-tolyl | Cu |
| 1-50 | —CH₂—CH₂— | Br | H | H | CH₃ | CH₃ | H | Me-Me-Me (Me) | o-tolyl | Cu |
| 1-51 | —CH₂—CH₂— | Br | H | H | H | Br | H | i-Pr, i-Pr | o-tolyl | Cu |

TABLE 1-continued
| Comp. | L¹ | R¹ | R² | R³ | R⁴ | R⁵ | R⁶ | R⁷ | A | M¹ |
|---|---|---|---|---|---|---|---|---|---|---|
| 1-52 | —CH₂—CH₂— | Br | H | H | H | Br | H | 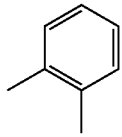 | 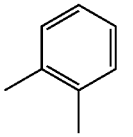 | Cu |
| 1-53 | —CH₂—CH₂— | Br | H | H | Br | Br | H | 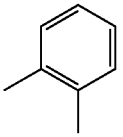 | 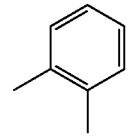 | Cu |
| 1-54 | —CH₂—CH₂— | Br | H | H | H | H | H | 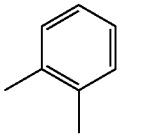 | 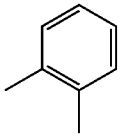 | Cu |
| 1-55 | —CH₂—CH₂— | Br | H | H | Br | H | H | | | Cu |
| 1-56 | —CH₂—CH₂— | Br | H | Br | Br | Br | Br | | | Cu |
| 1-57 | —CH₂— | H | H | H | H | H | H | | | Co |

TABLE 1-continued

| Comp. | L¹ | R¹ | R² | R³ | R⁴ | R⁵ | R⁶ | R⁷ | A | M¹ |
|---|---|---|---|---|---|---|---|---|---|---|
| 1-58 | —CH₂— | Br | H | H | Br | H | H | 3,5-dimethylphenyl | 2-methylphenyl | Zn |
| 1-59 | —CH₂— | H | H | H | H | Cl | H | 2-methoxyphenyl | 2,3-dimethyl-6-methoxyphenyl | Mn |
| 1-60 | —O— | H | H | Br | Br | Br | Br | 3,5-dimethylphenyl | 2-methylphenyl | Cu |
| 1-61 | —CH₂—CH₂— | Cl | H | H | Br | H | H | 3,5-dimethylphenyl | 2-methylphenyl | Cu |
| 1-62 | —CH₂—CH₂— | Cl | H | H | H | Cl | H | 3,5-dimethylphenyl | 3,5-dimethylphenyl | Cu |
| 1-63 | —CH₂—CH₂— | I | H | H | Cl | H | H | 2-methyl-5-isopropylphenyl (with 2-i-Pr) | 2-methylphenyl | Cu |

TABLE 1-continued
| Comp. | L¹ | R¹ | R² | R³ | R⁴ | R⁵ | R⁶ | R⁷ | A | M¹ |
|---|---|---|---|---|---|---|---|---|---|---|
| 1-64 | —CH₂—CH₂— | I | H | H | Br | Br | H | 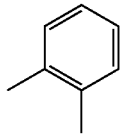 | 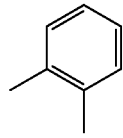 | Cu |
| 1-65 | —CH₂—CH₂— | Cl | CH₃ | H | H | H | H | 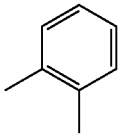 | 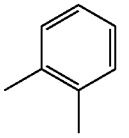 | Fe |
| 1-66 | —CH₂—CH₂— | Cl | H | H | H | C₂H₅ | H | 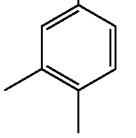 | 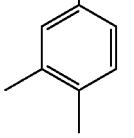 | Cu |
| 1-67 | —CH₂—CH₂— | Br | H | H | H | C₂H₅ | H | | | Co |
| 1-68 | —CH₂—CH₂— | Br | CH₃ | H | H | Br | H | | | Cu |
| 1-69 | —CH₂—CH₂— | CH₃ | H | H | Br | H | | | | Cu |

TABLE 1-continued

| Comp. | $L^1$ | $R^1$ | $R^2$ | $R^3$ | $R^4$ | $R^5$ | $R^6$ | $R^7$ | A | $M^1$ |
|---|---|---|---|---|---|---|---|---|---|---|
| 1-70 | —CH₂—CH₂— | CH₃ | H | Cl | Cl | Cl | Cl | 2,4,6-trimethylphenyl (Me, Me, Me) | 2-methylphenyl | Cu |
| 1-71 | —O— | Cl | CH₃ | H | H | H | H | 2-isopropyl-4-isopropyl-(with methyl) phenyl (i-Pr, i-Pr, Me) | 1-methylnaphthyl | Cu |
| 1-72 | —O— | H | H | H | H | Br | H | 2,4,6-trimethylphenyl (Me, Me, Me) | 2-methylphenyl | Co |
| 1-73 | —S— | H | H | H | H | H | H | 2,4-dimethylphenyl (Me, Me) | 4-methoxy-2-methylphenyl (OMe, Me) | Cu |
| 1-74 | —S— | Cl | H | H | Cl | H | H | 2,4,6-trimethylphenyl (Me, Me, Me) | 2-methylphenyl | Fe |
| 1-75 | —S— | H | H | Br | H | H | H | 2-isopropyl-4-isopropyl-(with methyl)phenyl (i-Pr, i-Pr, Me) | 4-methoxy-2-methylphenyl (OMe, Me) | Zn |

TABLE 1-continued
| Comp. | L¹ | R¹ | R² | R³ | R⁴ | R⁵ | R⁶ | R⁷ | A | M¹ |
|---|---|---|---|---|---|---|---|---|---|---|
| 1-76 | —CH₂—CH₂— | H | H | H | Br | H | H |  |  | Cu |
| 1-77 | —CH₂—CH₂— | H | H | H | H | Br | H |  |  | Cu |
| 1-78 | —CH₂—CH₂— | H | H | H | H | H | H |  |  | Cu |
| 1-79 | —CH₂—CH₂— | H | CH₃ | H | H | Br | H |  |  | Cu |
| 1-80 | —CH₂—CH₂— | H | H | H | Br | H | H |  |  | Cu |

TABLE 1-continued

| Comp. | L¹ | R¹ | R² | R³ | R⁴ | R⁵ | R⁶ | R⁷ | A | M¹ |
|---|---|---|---|---|---|---|---|---|---|---|
| 1-81 | —CH₂—CH₂— | H | CH₃ | H | H | Br | H | 3,5-dimethyl-4-methyl-(t-Bu)phenyl | 2-methylphenyl | Cu |
| 1-82 | —CH₂—CH₂— | H | CH₃ | H | Br | H | H | 3,5-dimethyl-4-methyl-(t-Bu)phenyl | 2,3-dimethylnaphthyl | Co |
| 1-83 | —CH₂—CH₂— | H | H | H | H | H | H | 3,5-dimethyl-4-methyl-(t-Bu)phenyl | 2-methylfuryl | Cu |
| 1-84 | —S— | H | Br | H | H | H | H | 3,5-di(i-Pr)-4-methylphenyl | 1,2-dimethyl-N-methylpyrrolyl | Cu |
| 1-85 | —CH₂—CH₂— | H | H | H | H | H | H | 3,5-dimethyl-4-methylphenyl | 2,5-dimethyl-3-methylthienyl | Co |

TABLE 1-continued

| Comp. | L¹ | R¹ | R² | R³ | R⁴ | R⁵ | R⁶ | R⁷ | A | M¹ |
|---|---|---|---|---|---|---|---|---|---|---|
| 1-86 | —CH₂—CH₂— | CH₃ | H | H | Br | H | H | 2,4-dimethylphenyl | 5,6-dimethylbenzoxazol-2-yl | Mn |
| 1-87 | —CH₂— | H | H | H | H | H | H | 4-bromo-2-(n-Hex)phenyl | 5,6-dimethylbenzoxazol-2-yl | Fe |
| 1-88 | —CH₂—CH₂— | I | H | H | H | H | H | phenyl | 2-methoxy-3-methylphenyl | Cu |
| 1-89 | —CH₂—CH₂— | I | H | H | O-n-Bu | H | H | phenyl | 2-methylphenyl | Co |
| 1-90 | —CH₂—CH₂— | I | H | H | H | H | H | OC₂H₅ | 2-methylphenyl | Ni |
| 1-91 | —CH₂—CH₂— | I | H | H | Br | H | H | 2,4,6-trimethylphenyl | 2-methylphenyl | Cu |

TABLE 1-continued
| Comp. | L¹ | R¹ | R² | R³ | R⁴ | R⁵ | R⁶ | R⁷ | A | M¹ |
|---|---|---|---|---|---|---|---|---|---|---|
| 1-92 | —CH₂—CH₂— | I | H | H | H | Br | H | 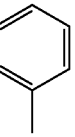 | 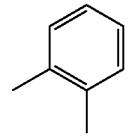 | Cu |
| 1-93 | —CH₂—CH₂— | I | H | H | Br | CH₃ | H | 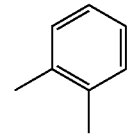 | 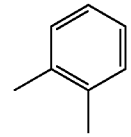 | Cu |
| 1-94 | —CH₂—CH₂— | I | H | H | H | OCH₃ | H | 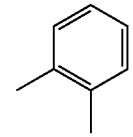 | 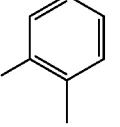 | Cu |
| 1-95 | —CH₂—CH₂— | I | H | H | CH₃ | CH₃ | H | | | Cu |
| 1-96 | —CH₂—CH₂— | I | H | H | H | Br | H | | | Cu |
| 1-97 | —CH₂—CH₂— | I | H | H | H | H | Br | | | Cu |

TABLE 1-continued

| Comp. | L¹ | R¹ | R² | R³ | R⁴ | R⁵ | R⁶ | R⁷ | A | M¹ |
|---|---|---|---|---|---|---|---|---|---|---|
| 1-98 | —CH₂—CH₂— | I | H | H | Br | Br | H | 2,4,6-trimethylphenyl | o-tolyl | Cu |
| 1-99 | —CH₂—CH₂— | I | H | H | H | H | H | 2,4,6-trimethylphenyl | o-tolyl | Cu |
| 1-100 | —CH₂—CH₂— | I | H | H | Br | H | H | 2-i-Pr-4-i-Pr-phenyl (2,4-di-i-Pr-tolyl) | o-tolyl | Cu |
| 1-101 | —CH₂—CH₂— | I | H | Br | Br | Br | Br | 2,4,6-trimethylphenyl | o-tolyl | Cu |
| 1-102 | —CH₂— | I | H | H | Br | H | H | 2,4,6-trimethylphenyl | o-tolyl | Zn |
| 1-103 | —CH₂—CH₂— | I | H | H | H | C₂H₅ | H | 2-i-Pr-4-i-Pr-phenyl | o-tolyl | Co |

TABLE 1-continued
| Comp. | L¹ | R¹ | R² | R³ | R⁴ | R⁵ | R⁶ | R⁷ | A | M¹ |
|---|---|---|---|---|---|---|---|---|---|---|
| 1-104 | —CH₂—CH₂— | I | CH₃ | H | H | Br | H | 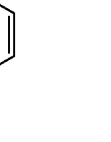 |  | Cu |
| 1-105 | —CH₂—CH₂— | I | H | H | I | H | H | 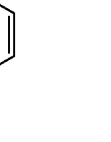 | 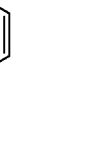 | Cu |
| 1-106 | —CH₂—CH₂— | I | H | H | H | I | H | 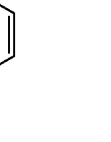 | 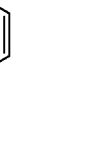 | Cu |
| 1-107 | —CH₂—CH₂— | Br | H | H | I | H | H | 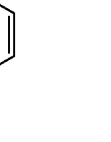 | 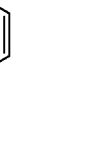 | Cu |
| 1-108 | —CH₂—CH₂— | Br | H | H | H | I | H | 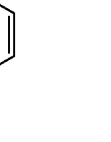 | 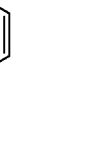 | Cu |

TABLE 1-continued

| Comp. | L¹ | R¹ | R² | R³ | R⁴ | R⁵ | R⁶ | R⁷ | A | M¹ |
|---|---|---|---|---|---|---|---|---|---|---|
| 1-109 | —CH₂—CH₂— | I | H | H | Cl | H | H | 3,5-di-Me-4-Me-phenyl | 2-Me-phenyl | Cu |
| 1-110 | —CH₂—CH₂— | I | H | H | H | Cl | H | 3,5-di-Me-4-Me-phenyl | 2-Me-phenyl | Cu |
| 1-111 | —CH₂—CH₂— | H | H | H | H | Br | H | 3,5-di-t-Bu-4-Me-phenyl | 2-Me-phenyl | Cu |
| 1-112 | —CH₂—CH₂— | Br | H | H | H | Cl | H | 3,5-di-Me-4-Me-phenyl | 2-Me-phenyl | Cu |

This invention will be more specifically described.

The term "optical recording medium" as used herein includes both an optical read-only medium exclusively for regenerating in which information has been recorded and an optical recording medium capable of recording and regenerating information, although herein the latter optical recording medium capable of recording and regenerating information, in particular, an optical recording medium comprising a recording layer and a reflecting layer on a substrate will be described as an appropriate example. An optical recording medium according to this invention has a laminated structure as illustrated in FIG. 1. Specifically, on a substrate 1 is formed a recording layer 2, on which is tightly formed a reflecting layer 3 and is then formed a substrate 5 via an adhesion layer 4. It may comprise another layer on the lower or upper side of the recording layer 2 or another layer on the upper side of the reflecting layer 3.

The substrates may be made of any material which is basically transparent at wavelengths of a recording and a regenerating beams; for example, acrylic resins such as polycarbonate resins, vinylchloride resins and poly(methyl methacrylate); polymer materials such as polystyrene resins and epoxy resins; and inorganic materials such as glass. The substrate material is shaped into a disc by, for example, injection molding. A guide groove or pit may be, if necessary, formed on the substrate surface. Such a guide groove or pit is desirably formed during shaping the substrate, but may be, alternatively formed on the substrate using an ultraviolet curing resin. When used as a DVD, the substrate is usually a disc with a thickness of about 1.2 mm and a diameter of 80 to 120 mm and having a hole with a diameter of about 15 mm in its center.

In this invention, a recording layer is formed on a substrate. The recording layer in this invention comprises a dipyrromethene-metal chelate represented by general formula (1) with $\lambda_{max}$ of about 450 nm to 630 nm, preferably a dipyrromethene-metal chelate represented by general formula (2), more preferably a dipyrromethene-metal chelate represented by general formula (3). In particular, it must have an optical constant suitable to a recording- or regenerating-laser wavelength from 520 nm to 690 nm (an optical constant is denoted as a complex refractive index (n+ki) wherein n and k are factors corresponding to a real and an imaginary components, respectively and n is a refractive index and k is an extinction coefficient).

An organic dye generally has a property that a refractive index n and an extinction coefficient k may significantly vary depending on a wavelength $\lambda$. If n is less than 1.8, a reflectance or signal modulation degree required for exact signal regenerating may not be obtained. If k is more than 0.40, a reflectance may be reduced to a level inadequate to give a good regenerating signal and also a signal may be too deteriorated to be practically used due to easy variation depending on a regenerating beam. In the light of the property, an organic dye having a preferable optical constant at a desired laser wavelength may be selected and used to deposit the recording layer for providing a medium with a higher reflectance and improved sensitivity.

A dipyrromethene-metal chelate compound represented by general formula (1) used in this invention has a higher absorption coefficient than a usual organic dye and its absorption wavelength band may be appropriately chosen by selecting a proper substituent may have an appropriate. It is, therefore, a considerably useful compound having an optical constant required for a recording layer at the above laser beam wavelength, i.e., n and k are 1.8 or more and 0.04 to 0.40, respectively, preferably n and k are 2.0 or more and 0.04 to 0.20, respectively.

In addition to the dipyrromethene-metal chelate compound represented by general formula (1), the recording layer in this invention may further comprise at least one dipyrromethene-metal chelate compound represented by general formula (4). There are no restrictions to a mixing ratio of these dipyrromethene-metal chelate compounds, but because of the above reasons, they are preferably mixed at a ratio giving an optical constant n of 1.8 or more, preferably 2.0 or more and k of 0.04 to 0.40, preferably 0.04 to 0.20.

(4)

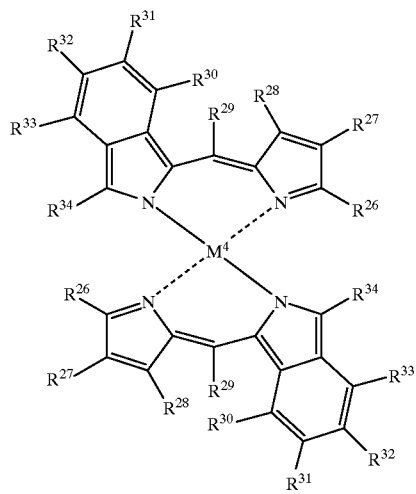

In this formula, $R^{26}$ to $R^{33}$ independently represent hydrogen, halogen, nitro, cyano, hydroxyl, amino, carboxyl, sulfo, substituted or unsubstituted alkyl with up to 20 carbon atoms, alkoxy, alkylthio, aryloxy, arylthio, alkenyl, acyl, alkoxycarbonyl, carbamoyl, acylamino, aralkyl, aryl or heteroaryl; $R^{34}$ represents halogen, substituted or unsubstituted aryl with up to 20 carbon atoms, heteroaryl, alkoxy, alkylthio, aryloxy or arylthio; and $M^4$ represents transition metal element.

There will be described a dipyrromethene-metal chelate compound represented by general formula (4) in addition to a dipyrromethene-metalchelate compound represented by general formula (1).

In general formula (4), examples of $R^{26}$ to $R^{33}$ are as defined for $R^1$ to $R^6$ in general formula (1), including hydrogen; halogens such as fluorine, chlorine, bromine and iodine; nitro; cyano; hydroxyl; amino; carboxyl; sulfo; the above substituted or unsubstituted alkyl with up to 20 carbon atoms; the above alkoxys; the above alkylthios; the above aryloxys; the above arylthios; the above alkenyls; the above acyls; the above alkoxycarbonyls; carbamoyl; the above acylaminos; the above aralkyls; the above aryls; and the above heteroaryls.

Examples of $R^{34}$ are as defined for $R^7$ in general formula (1), including the above halogens; the above aryls; the above heteroaryls; the above alkoxys; the above alkylthios; the above aryloxys; and the above arylthios.

$M^4$ may be any transition metal element capable of forming a chelate with a dipyrromethene compound, including the metals of Groups 8, 9, 10 (Group VIII), Group 11 (Group Ib), Group 12 (Group IIb), Group 3 (Group IIIa), Group 4 (Group IVa), Group 5 (Group Va), Group 6 (Group VIa) and Group 7 (Group VIIa), preferably nickel, cobalt, iron, ruthenium, rhodium, palladium, copper, osmium, iridium, platinumand zinc. In the light of light resistance, copper and cobalt are particularly preferable.

Table 2 shows examples of a dipyrromethene-metal chelate compound represented by general formula (4).

TABLE 2
| Comp. | $R^{26}$ | $R^{27}$ | $R^{28}$ | $R^{29}$ | $R^{30}$ | $R^{31}$ | $R^{32}$ | $R^{33}$ | $R^{34}$ | $M^4$ |
|---|---|---|---|---|---|---|---|---|---|---|
| 4-1 | 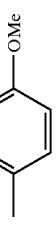 | H | H | H | H | H | Br | H | 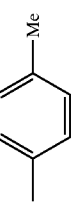 | Cu |
| 4-2 | 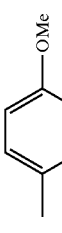 | H | H | H | H | H | Br | H | 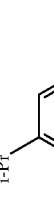 | Cu |
| 4-3 | CH$_3$ | C$_2$H$_5$ | CH$_3$ | H | H | H | H | H | 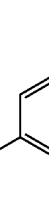 | Cu |
| 4-4 |  | H | H | H | H | H | Br | H |  | Cu |
| 4-5 |  | H | H | H | H | H | H | H | 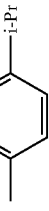 | Cu |
| 4-6 | 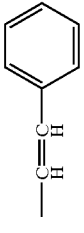 | H | 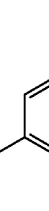 | H | H | H | H | H | 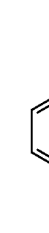 | Cu |
| 4-7 |  | H | H | H | H | Cl | Cl | H | (Me,Me phenyl) | Cu |

TABLE 2-continued

| Comp. | R$^{26}$ | R$^{27}$ | R$^{28}$ | R$^{29}$ | R$^{30}$ | R$^{31}$ | R$^{32}$ | R$^{33}$ | R$^{34}$ | M$^4$ |
|---|---|---|---|---|---|---|---|---|---|---|
| 4-8 | *p*-tolyl | H | *p*-tolyl | H | H | Cl | H | H | 2-i-Pr-5-i-Pr-phenyl (2-i-Pr, 4-i-Pr) | Cu |
| 4-9 | H | C$_2$H$_5$ | C$_2$H$_5$ | CH$_3$ | Cl | Cl | Cl | Cl | Br | Ni |
| 4-10 | CH$_3$ | H | CH$_3$ | H | H | NO$_2$ | H | H | phenyl | Zn |
| 4-11 | 4-MeO-phenyl | Br | 4-MeO-phenyl | H | H | H | OH | H | 2,4-diMe-phenyl | Co |
| 4-12 | —CH=CHCH$_2$ | H | H | H | H | H | NHCOCH$_3$ | H | 2-i-Pr-5-i-Pr-phenyl (2-i-Pr, 4-i-Pr) | Mn |
| 4-13 | PhCH=CH— | H | Br | CN | H | H | H | H | 2,5-diMe-3-Et-4-Me-pyrrole (NH) | Mn |
| 4-14 | H | H | OC$_2$H$_5$ | H | H | Br | H | H | Br | Cu |
| 4-15 | CH$_3$ | C$_2$H$_5$ | CH$_3$ | C$_2$H$_5$ | H | CO$_2$H | H | H | phenyl | Co |
| 4-16 | CH$_3$ | C$_2$H$_5$ | SC$_2$H$_5$ | CH$_3$ | H | Br | Br | H | Cl | Co |

TABLE 2-continued

| Comp. | $R^{26}$ | $R^{27}$ | $R^{28}$ | $R^{29}$ | $R^{30}$ | $R^{31}$ | $R^{32}$ | $R^{33}$ | $R^{34}$ | $M^4$ |
|---|---|---|---|---|---|---|---|---|---|---|
| 4-17 | 1-methyl-2-pyrrolyl | H | 1-methyl-2-pyrrolyl | H | H | $NH_2$ | H | H | $OC_6H_5$ | Cu |
| 4-18 | phenyl | H | 4-methoxyphenyl | H | H | Br | H | H | $SC_2H_5$ | Co |
| 4-19 | phenylthio | H | H | H | H | Cl | H | H | phenyl | Zn |
| 4-20 | phenyl | benzyl | phenyl | $CH_3$ | H | Cl | Cl | H | Cl | Ni |
| 4-21 | $CH_3$ | H | Br | $CH_3$ | H | $CO_2CH_3$ | H | H | 2-isopropyl-4-methylphenyl (with i-Pr) | Cu |
| 4-22 | 4-(dimethylamino)phenyl | H | $COCH_3$ | H | H | H | $CONH_2$ | H | 4-ethoxyphenyl ($OC_2H_5$) | Mn |
| 4-23 | 4-methylphenyl | H | H | H | $CH_3$ | $SO_3H$ | H | $CH_3$ | phenylthio (S-Ph) | Ni |
| 4-24 | $CH_3$ | 1-methyl-2-pyrrolyl | $CH_3$ | H | H | Br | H | H | 4-methylphenyl | Cu |

The compounds may be blended with a dye other than those described above having a local absorption maximum at a wavelength of 450 nm to 630 nm and having a large refractive index at a wavelength of 520 nm to 690 nm. Examples of such a dye include cyanine dyes, squarylium dyes, naphthoquinone dyes, anthraquinone dyes, porphyrin dyes, azaporphyrin dyes, tetrapiraporphyrazine dyes, indophenol dyes, pyrylium dyes, thiopyrylium dyes, azulenium dyes, triphenylmethane dyes, xanthene dyes, indathlene dyes, indigo dyes, thioindigo dyes, melocyanine dyes, thiazine dyes, acridine dyes and oxadine dyes, which may be used alone or in combination of two or more. A mixing proportion of these dyes is generally about 0.1 to 30 wt % to a dipyrromethene-metal chelate compound represented by general formula (1).

When the dipyrromethene-metal chelate compound represented by general formula (1) has a small k value to a recording or regenerating laser wavelength selected from the range of 520 nm to 690 nm, a light-absorptive compound with a local absorption maximum at a wavelength of 600 nm to 900 nm may be added for improving, for example, recording properties. Examples of such an additional compound include cyanine dyes, squarylium dyes, naphthoquinone dyes, anthraquinone dyes, porphyrin dyes, azaporphyrin dyes, tetrapiraporphyrazine dyes, indophenol dyes, pyrylium dyes, thiopyrylium dyes, azulenium dyes, triphenylmethane dyes, xanthene dyes, indathlene dyes, indigo dyes, thioindigo dyes, melocyanine dyes, thiazine dyes, acridine dyes, oxadine dyes, phthalocyanine dyes and naphthalocyanine dyes, and a combination of two or more. A mixing proportion of these dyes is about 0.1 to 30 wt % to the dipyrromethene-metal chelate compound represented by general formula (1).

Basically, a reflectance of 20% may allow an optical recording medium of this invention to be regenerated with a laser beam with a wavelength in the range of 520 nm to 690 nm to some extent, and are flectance of 30% or more is preferable.

When forming a recording layer, the above dye may be, if necessary, combined with a quencher, a dye-degradation accelerator, an ultraviolet absorber, an adhesive or an endothermic degradable compound, or may have a moiety having such an effect as a substituent.

Preferable examples of a quencher include metal complexes of acetylacetonates; bisdithiols such as bisdithio-a-diketones and bisphenyldithiols; thiocathecols, salicylaldehyde oximes and thiobisphenolates. Amines are also preferable.

Examples of a thermal degradation accelerator include metal compounds such as metal antiknock agents, metallocene compounds and acetylacetonate-metal complexes.

Furthermore, if necessary, a binder, leveling agent or an antifoaming agent may be combined. Preferable examples of a binder include polyvinyl alcohol, polyvinylpyrrolidone, nitrocellulose, cellulose acetate, ketone resins, acrylic resins, polystyrene resins, urethane resins, polyvinyl butyral, polycarbonate and polyolefins.

When depositing a recording layer on a substrate, a layer made of an inorganic compound or a polymer may be formed on the substrate for improving solvent resistance of the substrate, a reflectance or recording sensitivity.

A content of the dipyrromethene-metal chelate compound represented by general formula (1) in the recording layer is 30 wt % or more, preferably 60 wt % or more. Further, it may be preferable that the content is substantially 100 wt %.

The recording layer may be formed by, for example, application methods such as spin coating, spraying, casting and dipping; sputtering; chemical vapor deposition and vacuum deposition, preferably spin coating because of its convenience.

When using an application method such as spin coating, a dipyrromethene-metal chelate compound represented by general formula (1) or (2) is dissolved or dispersed in a solvent to 1 to 40 wt %, preferably 3 to 30 wt %. The solvent is preferably selected from those which are not harmful to a substrate. Examples of such a solvent include alcoholic solvents such as methanol, ethanol, isopropyl alcohol, octafluoropentanol, allyl alcohol, methylcellosolve, ethylcellosolve and tetrafluoropropanol; aliphatic or alicyclic hydrocarbon solvents such as hexane, heptane, octane, decane, cyclohexane, methylcyclohexane, ethylcyclohexane and dimethylcyclohexane; aromatic hydrocarbon solvents such as toluene, xylenes and benzene; halogenated hydrocarbon solvents such as carbon tetrachloride, chloroform, tetrachloroethane and dibromoethane; ether solvents such as diethyl ether, dibutyl ether, diisopropyl ether and dioxane; ketone solvents such as acetone and 3-hydroxy-3-methyl-2-butanone; ester solvents such as ethyl acetate and methyl lactate; and water, which may be used alone or in combination of two or more.

If necessary, a dye for the recording layer may be dispersed in a polymer film.

When a solvent unharmful to a substrate cannot be selected, sputtering, chemical vapor deposition or vacuum deposition may be effective.

A thickness of the dye layer is preferably, but not limited to, 50 nm to 300 nm. If the thickness of the dye layer is less than 50 nm, recording may not be performed due to excessive thermal diffusion or a recording signal may be distorted and have a reduced amplitude. If it is more than 300 nm, a reflectance may be reduced, leading to deteriorate regenerating-signal properties.

Then, on the recording layer is formed a reflecting layer with a thickness of preferably 50 nm to 300 nm. The reflecting layer may be made of a material exhibiting an adequately high reflectance at a wavelength of regenerating light; for example, metals such as Au, Al, Ag, Cu, Ti, Cr, Ni, Pt, Ta, Cr and Pd may be used alone or as an alloy. Among these, Au, Al and Ag are suitable as a reflecting layer material because of their higher reflectance. Besides these, the reflecting layer may comprise another metal or metalloid such as Mg, Se, Hf, V, Nb, Ru, W, Mn, Re, Fe, Co, Rh, Ir, Zn, Cd, Ga, In, Si, Ge, Te, Pb, Po, Sn and Bi. A material comprising Au as a main component is suitable because it may easily provide a reflecting layer with a higher reflectance. A main component used herein refers to a component contained in a content of 50% or more. It may be possible to alternately laminate lower refractive index films and higher refractive index films made of materials other than a metal to form a multilayer film used as a reflecting layer.

The reflecting layer may be formed by, for example, sputtering, ion plating, chemical vapor deposition or vacuum deposition. An intermediate layer or adhesion layer made of a known inorganic or organic material may be formed on the substrate or under the reflecting layer for improving a reflectance, recording properties or adhesiveness.

There are no restrictions to a material for a protective layer on the reflecting layer as long as it may protect the reflecting layer from external force. Examples of an organic substance used include thermoplastic resins, thermosetting resins, electron-beam curing resin and ultraviolet curing resins. Examples of an inorganic material used include $SiO_2$, $Si_3N_4$, $MgF_2$ and $SnO_2$. A thermoplastic or thermosetting resin may be dissolved in an appropriate solvent, applied and dried to give a film. An ultraviolet curing resin may be applied as it is or after preparing an application solution by dissolving it in an appropriate solvent and cured by irradiation of ultraviolet rays to give a film. Examples of an ultraviolet curing resin which may be used include acrylate resins such as urethane acrylate, epoxyacrylate and polyester acrylate. These materials may be used alone or in combination of two or more and may be also used not only as a monolayer film but also as a multilayer film.

The protective layer may be formed, as described for the recording layer, by, for example, an application method such as spin coating and casting; sputtering; and chemical vapor deposition, preferably spin coating.

A thickness of the protective layer is generally 0.1 μm to 100 μm, 3 μm to 30 μm in this invention, more preferably 5 μmm to 20 μm.

on the above-mentioned protective layer, a label and the like can also be further printed. In addition, there may be employed a means of laminating a protective sheet or a substrate on the surface of the reflective layer, or another means of each reflective layer of two optical recording media may come in contact with each other to fix two optical recording media. For the purpose of protecting the surface or preventing the deposition of dust or the like, an ultraviolet curing resin layer, an inorganic thin film or the like may be formed on the mirror surface of the substrate.

A laser with a wavelength of 520 nm to 690 nm herein is for example, but not limited to, a dye laser whose wavelength may be selected in a wide visible-light range, a helium-neon laser with a wavelength of 633 nm, a high-output semiconductor layer with a wavelength of about 680, 650 or 635 nm which has been recently developed and a harmonic-converted YAG laser with a wavelength of 532 nm. This invention may achieve higher-density recording and regenerating at one wavelength or multiple wavelengths selected from these.

This invention will be described with reference to, but not limited to, Examples.

EXAMPLE 1

Preparation of a Dipyrromethene-metal Chelate Compound (1-1)

In 200 mL of ethanol was dissolved 3.79 g of the compound represented by structural formula (7-a) and 2.10 g of the compound represented by structural formula (8-a). To the solution was added dropwise 2.07 g of 47% hydrobromic acid, and the mixture was stirred at room temperature for 2 hours. After concentration in vacuo, the residue was extracted with 200 mL of chloroform and washed with water. The organic layer was separated and evaporated to give 4.90 g of the compound represented by structural formula (9-a).

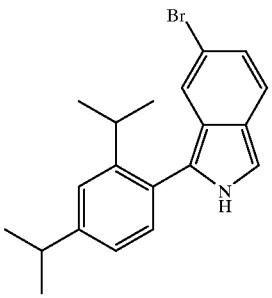

(7-a)

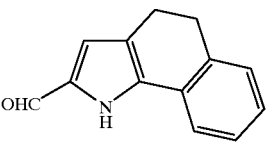

(8-a)

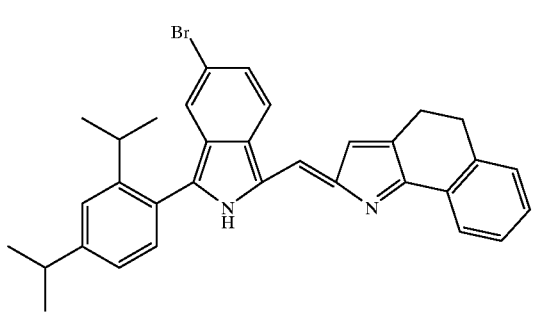

(9-a)

Then, in 200 mL of ethanol is dissolved 3.50 g of the compound represented by structural formula (9-a) and after adding 0.95 g of copper acetate the mixture was refluxed with stirring for 2 hours. After concentration in vacuo, the precipitate was collected by filtration and washed with methanol and water to give 1.50 g of the compound represented by structural formula (1-1).

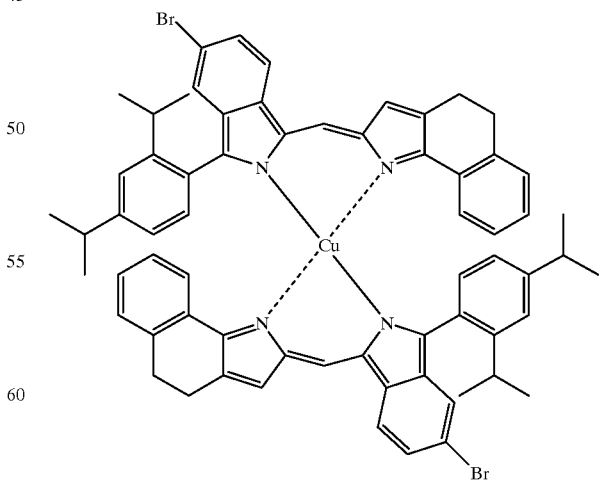

(1-1)

From the following analysis results, it was identified as the title compound.

| Elementary analysis: $C_{66}H_{60}N_4Br_2Cu$ | | | |
|---|---|---|---|
| | C | H | N |
| Calcd. (%) | 69.99 | 5.34 | 4.95 |
| Found (%) | 70.01 | 5.49 | 4.93 |

MS (m/e): 1132 (M⁺)

A solution of the compound thus obtained in toluene exhibited a local absorption maximum at 609 nm and a gram absorption coefficient of $1.05 \times 10^5$ mL/g*cm.

EXAMPLE 2

Preparation of a Dipyrromethene-metal Chelate Compound (1-4)

In 150 mL of ethanol was dissolved 2.80 g of the compound represented by structural formula (7-b) and 1.77 g of the compound represented by structural formula (8-a). To the solution was added dropwise 1.70 g of 47% hydrobromic acid, and the mixture was stirred at room temperature for 3 hours. After concentration in vacuo, the residue was extracted with 200 mL of chloroform and washed with water. The organic layer was separated and evaporated to give 3.88 g of the compound represented by structural formula (9-b).

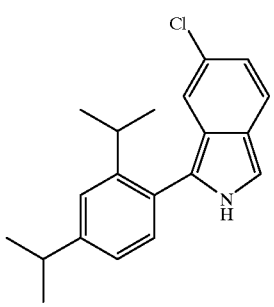

(7-b)

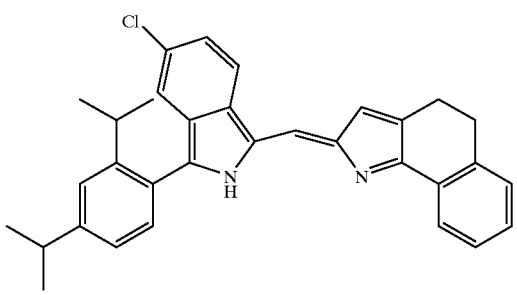

(9-b)

Then, in 150 mL of ethanol is dissolved 3.70 g of the compound represented by structural formula (9-b) and after adding 1.09 g of copper acetate the mixture was refluxed with stirring for 2 hours. After concentration in vacuo, the precipitate was collected by filtration and washed with methanol and water to give 2.67 g of the compound represented by structural formula (1-4).

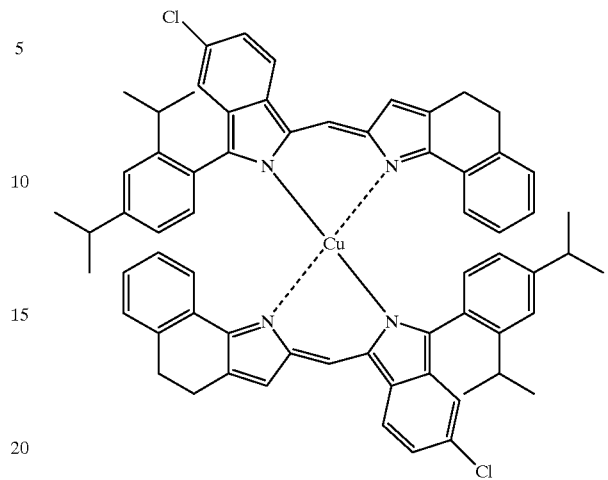

(1-4)

From the following analysis results, it was identified as the title compound.

| Elementary analysis: $C_{66}H_{60}N_4Cl_2Cu$ | | | |
|---|---|---|---|
| | C | H | N |
| Calcd. (%) | 75.95 | 5.79 | 5.37 |
| Found (%) | 75.90 | 5.65 | 5.41 |

MS (m/e): 1043 (M⁺)

A solution of the compound thus obtained in toluene exhibited a local absorption maximum at 609 nm and a gram absorption coefficient of $1.15 \times 10^5$ mL/g*cm.

EXAMPLE 3

Preparation of a Dipyrromethene-metal Chelate Compound (1-6)

In 100 mL of ethanol was dissolved 2.10 g of the compound represented by structural formula (7-c) and 1.38 g of the compound represented by structural formula (8-a). To the solution was added dropwise 1.45 g of 47% hydrobromic acid, and the mixture was stirred at room temperature for 3 hours. After concentration in vacuo, the residue was extracted with 150 mL of chloroform and washed with water. The organic layer was separated and evaporated to give 2.62 g of the compound represented by structural formula (9-c).

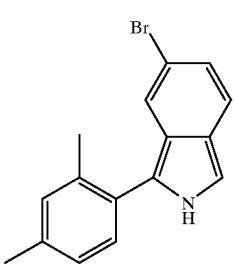

(7-c)

-continued (9-c)

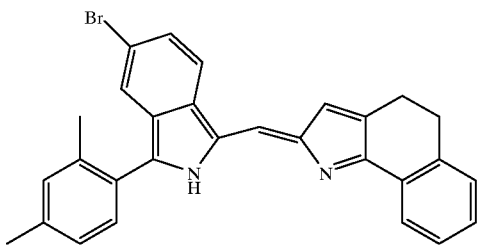

Then, in 100 mL of ethanol is dissolved 2.05 g of the compound represented by structural formula (9-c) and after adding 0.70 g of copper acetate the mixture was refluxed with stirring for 3 hours. After concentration in vacuo, the precipitate was collected by filtration and washed with methanol and water to give 1.53 g of the compound represented by structural formula (1-6).

(1-6)

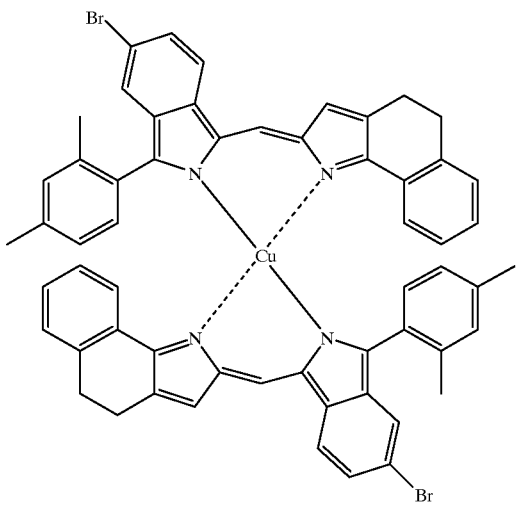

From the following analysis results, it was identified as the title compound.

| Elementary analysis: $C_{58}H_{44}N_4Br_2Cu$ | | | |
|---|---|---|---|
| | C | H | N |
| Calcd. (%) | 68.27 | 4.35 | 5.49 |
| Found (%) | 68.19 | 4.40 | 5.58 |

MS (m/e): 1020 (M⁺)

A solution of the compound thus obtained in toluene exhibited a local absorption maximum at 605.5 nm and a gram absorption coefficient of $1.20 \times 10^5$ mL/g*cm.

EXAMPLE 4

Preparation of a Dipyrromethene-metal Chelate Compound (1-10)

In 200 mL of ethanol was dissolved 3.00 g of the compound represented by structural formula (7-d) and 1.91 g of the compound represented by structural formula (8-b). To the solution was added dropwise 1.59 g of 47% hydrobromic acid, and the mixture was stirred at room temperature for 3 hours. After concentration in vacuo, the residue was extracted with 200 mL of chloroform and washed with water. The organic layer was separated and evaporated to give 3.12 g of the compound represented by structural formula (9-d).

(7-d)

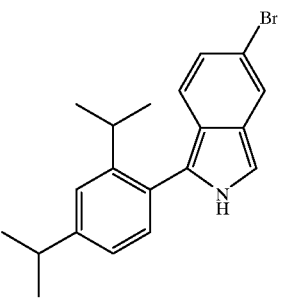

(8-b)

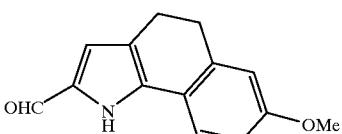

(9-d)

Then, in 200 mL of ethanol is dissolved 3.05 g of the compound represented by structural formula (9-d) and after adding 1.34 g of nickel acetate tetrahydrate the mixture was refluxed with stirring for 2 hours. After concentration in vacuo, the precipitate was collected by filtration and washed with methanol and water to give 1.86 g of the compound represented by structural formula (1-10).

(1-10)

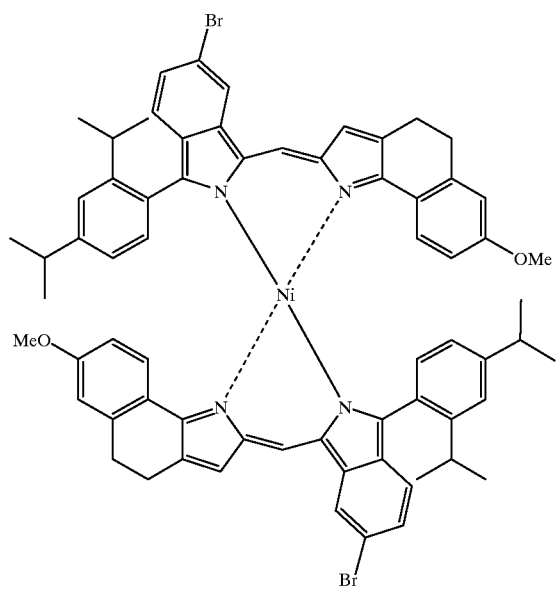

From the following analysis results, it was identified as the title compound.

Elementary analysis: $C_{68}H_{64}N_4O_2Br_2Ni$

|  | C | H | N |
|---|---|---|---|
| Calcd. (%) | 68.76 | 5.43 | 4.72 |
| Found (%) | 68.71 | 5.51 | 4.75 |

MS (m/e): 1187 (M⁺)

A solution of the compound thus obtained in toluene exhibited a local absorption maximum at 612 nm and a gram absorption coefficient of $1.09 \times 10^5$ mL/g*cm.

EXAMPLE 5

Preparation of a Dipyrromethene-metal Chelate Compound (1-27)

In 120 mL of ethanol was dissolved 2.65 g of the compound represented by structural formula (5-a) and 1.31 g of the compound represented by structural formula (6-a). To the solution was added dropwise 1.33 g of 47% hydrobromic acid, and the mixture was stirred at room temperature for 2 hours. After concentration in vacuo, the residue was extracted with 200 mL of chloroform and washed with water. The organic layer was separated and evaporated to give 2.48 g of the compound represented by structural formula (9-e).

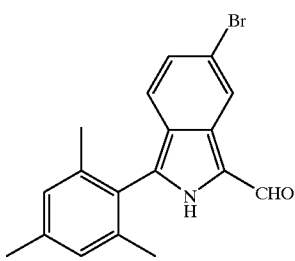
(5-a)

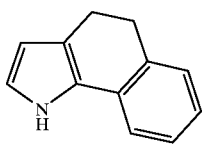
(6-a)

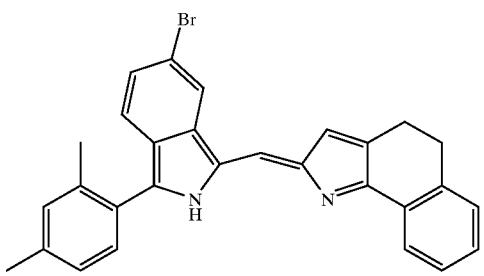
(9-e)

Then, in 150 mL of ethanol is dissolved 2.30 g of the compound represented by structural formula (9-e) and after adding 0.54 g of cobalt chloride the mixture was refluxed with stirring for 2 hours. After concentration in vacuo, the precipitate was collected by filtration and washed with methanol and water to give 2.17 g of the compound represented by structural formula (1-27).

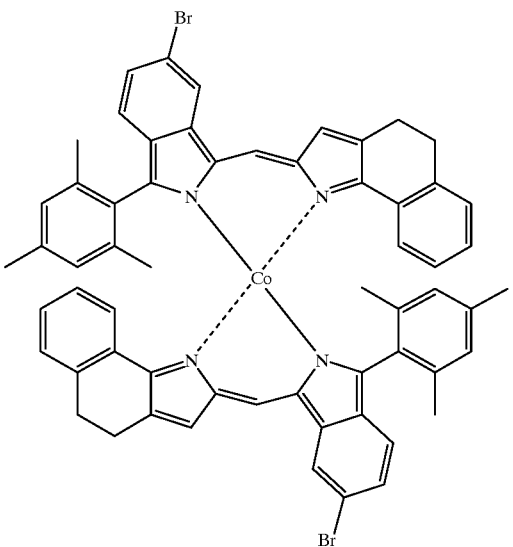
(1-27)

From the following analysis results, it was identified as the title compound.

Elementary analysis: $C_{60}H_{48}N_4Br_2Co$

|  | C | H | N |
|---|---|---|---|
| Calcd. (%) | 69.04 | 4.64 | 5.37 |
| Found (%) | 69.02 | 4.71 | 5.40 |

MS (m/e): 1043 (M⁺)

A solution of the compound thus obtained in toluene exhibited a local absorption maximum at 608 nm and a gram absorption coefficient of $1.19 \times 10^5$ mL/g*cm.

EXAMPLE 6

Preparation of a Dipyrromethene-metal Chelate Compound (1-46)

In 300 mL of ethanol was dissolved 3.14 g of the compound represented by structural formula (7-e) and 2.76 g of the compound represented by structural formula (8-c). To the solution was added dropwise 1.72 g of 47% hydrobromic acid, and the mixture was stirred at room temperature for 3 hours. After concentration in vacuo, the residue was extracted with 200 mL of chloroform and washed with water. The organic layer was separated and evaporated to give 4.55 g of the compound represented by structural formula (9-f).

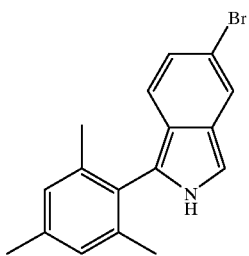
(7-e)

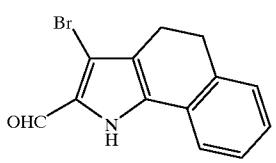
(8-c)

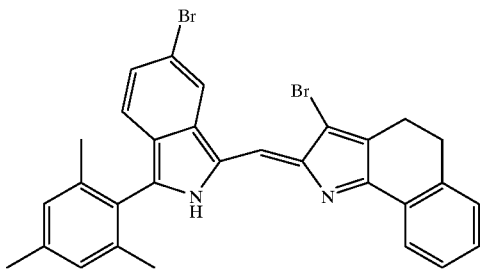
(9-f)

Then, in 200 mL of ethanol is dissolved 3.43 g of the compound represented by structural formula (9-f) and after adding 1.09 g of copper acetate the mixture was refluxed with stirring for 2 hours. After concentration in vacuo, the precipitate was collected by filtration and washed with methanol and water to give 2.81 g of the compound represented by structural formula (1-46).

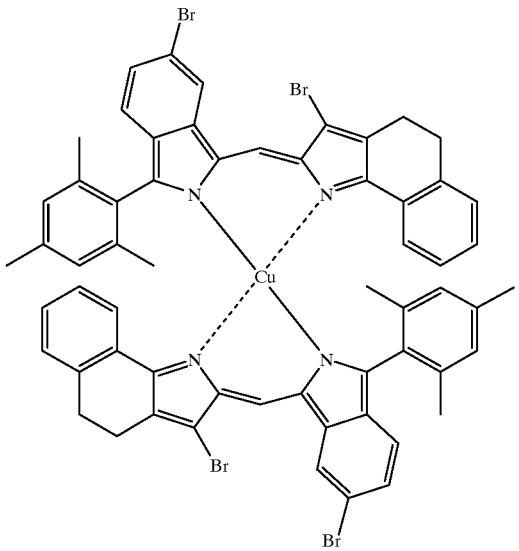
(1-46)

From the following analysis results, it was identified as the title compound.

| Elementary analysis: $C_{60}H_{46}N_4Br_4Cu$ | | | |
|---|---|---|---|
| | C | H | N |
| Calcd. (%) | 59.75 | 3.84 | 4.64 |
| Found (%) | 59.71 | 3.97 | 4.69 |

MS (m/e): 1206 (M⁺)

A solution of the compound thus obtained in toluene exhibited a local absorption maximum at 592.5 nm and a gram absorption coefficient of $1.22 \times 10^5$ mL/g*cm.

EXAMPLE 7

Preparation of a Dipyrromethene-metal Chelate Compound (1-48)

In 300 mL of ethanol was dissolved 2.24 g of the compound represented by structural formula (7-f) and 2.49 g of the compound represented by structural formula (8-c). To the solution was added dropwise 1.55 g of 47% hydrobromic acid, and the mixture was stirred at room temperature for 3 hours. After concentration in vacuo, the residue was extracted with 200 mL of chloroform and washed with water. The organic layer was separated and evaporated to give 3.15 g of the compound represented by structural formula (9-g).

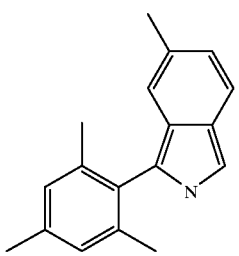
(7-f)

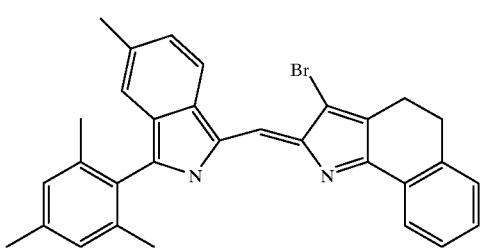
(9-g)

Then, in 200 mL of ethanol is dissolved 3.00 g of the compound represented by structural formula (9-g) and after adding 1.07 g of copper acetate the mixture was refluxed with stirring for 2 hours. After concentration in vacuo, the precipitate was collected by filtration and washed with methanol and water to give 2.64 g of the compound represented by structural formula (1-48).

(1-48)

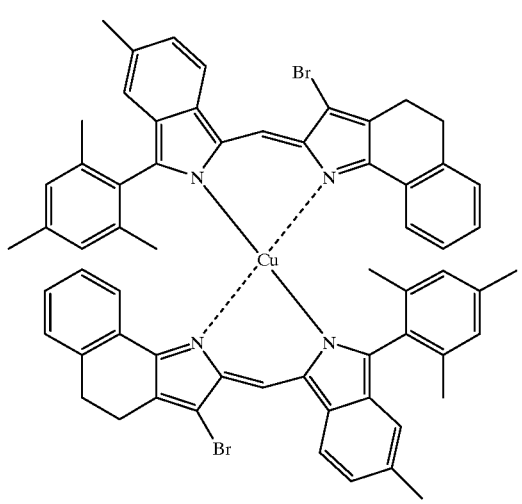

From the following analysis results, it was identified as the title compound.

Elementary analysis: $C_{62}H_{52}N_4Br_2Cu$

|  | C | H | N |
|---|---|---|---|
| Calcd. (%) | 69.18 | 4.87 | 5.20 |
| Found (%) | 69.15 | 4.91 | 5.21 |

MS (m/e): 1076 (M⁺)

A solution of the compound thus obtained in toluene exhibited a local absorption maximum at 591 nm and a gram absorption coefficient of $1.17 \times 10^5$ mL/g*cm.

EXAMPLE 8

Preparation of a Dipyrromethene-metal Chelate Compound (1-79)

In 300 mL of ethanol was dissolved 2.67 g of the compound represented by structural formula (7-g) and 1.80 g of the compound represented by structural formula (8-d). To the solution was added dropwise 1.46 g of 47% hydrobromic acid, and the mixture was stirred at room temperature for 3 hours. After concentration in vacuo, the residue was extracted with 200 mL of chloroform and washed with water. The organic layer was separated and evaporated to give 2.58 g of the compound represented by structural formula (9-h).

(7-g)

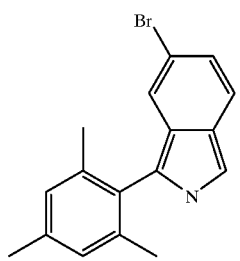

(8-d)

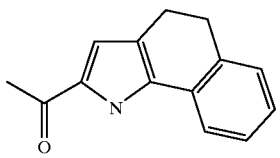

(9-h)

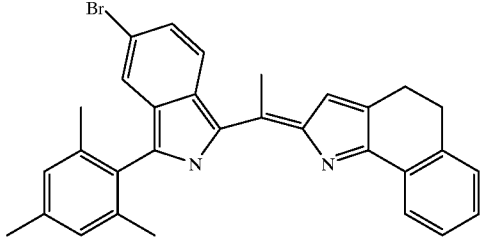

Then, in 200 mL of ethanol is dissolved 2.35 g of the compound represented by structural formula (9-h) and after adding 0.84 g of copper acetate the mixture was refluxed with stirring for 2 hours. After concentration in vacuo, the precipitate was collected by filtration and washed with methanol and water to give 1.92 g of the compound represented by structural formula (1-79).

(1-79)

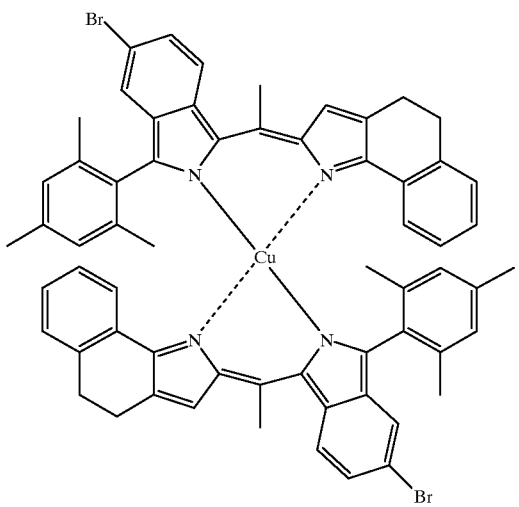

From the following analysis results, it was identified as the title compound.

Elementary analysis: $C_{62}H_{52}N_4Br_2Cu$

|  | C | H | N |
|---|---|---|---|
| Calcd. (%) | 69.18 | 4.87 | 5.20 |
| Found (%) | 69.20 | 4.82 | 5.17 |

MS (m/e): 1076 (M⁺)

A solution of the compound thus obtained in toluene exhibited a local absorption maximum at 596 nm and a gram absorption coefficient of $1.46 \times 10^5$ mL/g*cm.

EXAMPLE 9

In 10 mL of dimethylcyclohexane was dissolved 0.2 g of the dipyrromethene-metal chelate compound (1-1) to prepare a dye solution. A substrate used was a disc made of a polycarbonate resin having a continuous guide groove (track pitch: 0.74 µm) whose diameter and thickness were 120 mm and 0.6 mm, respectively.

On the substrate was spin-coated the dye solution at a revolution speed of 1500 rpm, and the substrate was dried at 70° C. for 3 hours to form a recording layer. Optical constants of this recording layer at 640 nm, 650 nm and 660 nm were as follows.

|   | 640 nm | 650 nm | 660 nm |
|---|--------|--------|--------|
| n | 2.60   | 2.39   | 2.24   |
| k | 0.33   | 0.14   | 0.09   |

On the recording layer was deposited Au by sputtering using a sputtering equipment (CDI-900; Baruzas Co.) to form a reflecting layer with a thickness of 100 nm. Argon gas was used as a sputtering gas. The sputtering conditions were a sputtering power of 2.5 kW and a sputtering gas pressure of 1.33 Pa ($1.0 \times 10^{-2}$ Torr).

On the reflecting layer was spin-coated an ultraviolet curing resin SD-1700 (Dainippon Ink And Chemicals, Inc.) and the resin layer was irradiated with ultraviolet rays to form a protective layer with a thickness of 6 µm.

On the protective layer was spin-coated an ultraviolet curing adhesive SD-301 (Dainippon Ink And Chemicals, Inc.). On the adhesive was placed a disc substrate made of a polycarbonate resin with a diameter of 120 mm and a thickness of 0.6 mm, and the product was irradiated with ultraviolet rays to provide a laminated optical recording medium.

On the optical recording medium thus prepared, recording was performed with a linear velocity of 3.5 m/s and the shortest pit length of 0.40 µm at a wavelength of 658 nm using an optical disc evaluator equipped with a semiconductor laser head whose lens numerical aperture was 0.6 (DDU-1000; PULSTEC INDUSTRIAL CO., LTD) and a pulse generator (PULSTEC INDUSTRIAL CO., LTD). A recording sensitivity was 9.5 m/W. After recording, a signal was regenerated using an evaluation device equipped with a 650 nm red semiconductor laser head with a lens numerical aperture of 0.6 to determine a reflectance, a jitter and a modulation degree. The results were satisfactory; a reflectance: 49.5%, a jitter: 7.5% and a modulation degree: 0.60 in regeneration at 650 nm. The medium exhibited no changes after a light resistance test with a carbon arc for 100 hours and a humidity and heat-resistance test at 80° C. and 85% for 100 hours. Even after regeneration by 1 million cycles with a regenerating beam of 0.7 mW, the jitter varied only by 1% or less.

Furthermore, recording was performed with a linear velocity of 7.0 m/s (double-speed recording) and the shortest pit length of 0.40 µm, resulting in a recording sensitivity of 13.5 mW. After recording, a signal was regenerated using an evaluation device equipped with a 650 nm red semiconductor laser head with a lens numerical aperture of 0.6 to determine a reflectance, a jitter and a modulation degree. The results were satisfactory; a reflectance: 45.5%, a jitter: 7.9% and a modulation degree: 0.60 in regeneration at 650 nm.

EXAMPLE 10

An optical recording medium was prepared as described in Example 9, except that 0.2 g of the dipyrromethene-metal chelate compound (1-4) was dissolved in 10 mL of dimethylcyclohexane to prepare a dye solution. Optical constants of this recording layer at 640 nm, 650 nm and 660 nm were as follows.

|   | 640 nm | 650 nm | 660 nm |
|---|--------|--------|--------|
| n | 2.62   | 2.41   | 2.26   |
| k | 0.32   | 0.12   | 0.07   |

As described in Example 6, on the optical recording medium thus prepared, recording was performed with a linear velocity of 3.5 m/s and the shortest pit length of 0.40 µm at a wavelength of 658 nm using an optical disc evaluator equipped with a semiconductor laser head whose lens numerical aperture was 0.6 (DDU-1000; PULSTEC INDUSTRIAL Co., LTD) and a pulse generator (PULSTEC INDUSTRIAL CO., LTD). A recording sensitivity was 9.5 m/W. After recording, a signal was regenerated using an evaluation device equipped with a 650 nm red semiconductor laser head with a lens numerical aperture of 0.6 to determine a reflectance, a jitter and a modulation degree. The results were satisfactory; a reflectance: 47.4%, a jitter: 7.7% and a modulation degree: 0.63 in regeneration at 650 nm. The medium exhibited no changes after a light resistance test with a carbon arc for 100 hours and a humidity and heat-resistance test at 80° C. and 85% for 100 hours. Even after regeneration by 1 million cycles with a regenerating beam of 0.7 mW, the jitter varied only by 1% or less.

Furthermore, recording was performed with a linear velocity of 7.0 m/s (double-speed recording) and the shortest pit length of 0.40 µm, resulting in a recording sensitivity of 13.0 mw. After recording, a signal was regenerated using an evaluation device equipped with a 650 nm red semiconductor laser head with a lens numerical aperture of 0.6 to determine a reflectance, a jitter and a modulation degree. The results were satisfactory; a reflectance: 46.0%, a jitter: 8.0% and a modulation degree: 0.60 in regeneration at 650 nm.

EXAMPLE 11

An optical recording medium was prepared as described in Example 9, except that 0.2 g of the dipyrromethene-metal chelate compound (1-8) was dissolved in 10 mL of dimethylcyclohexane to prepare a dye solution. Optical constants of this recording layer at 640 nm, 650 nm and 660 nm were as follows.

|   | 640 nm | 650 nm | 660 nm |
|---|--------|--------|--------|
| n | 2.27   | 2.18   | 2.09   |
| k | 0.08   | 0.05   | 0.04   |

On the optical recording medium thus prepared, recording was performed with a linear velocity of 3.5 m/s and the shortest pit length of 0.40 µm at a wavelength of 639 nm using an optical disc evaluator equipped with a semiconductor laser head whose lens numerical aperture was 0.6 (DDU-1000; PULSTEC INDUSTRIAL CO., LTD) and a pulse generator (PULSTEC INDUSTRIAL CO., LTD). A recording sensitivity was 9.5 m/W. After recording, a signal was regenerated using an evaluation device equipped with a 650 nm red semiconductor laser head with a lens numerical aperture of 0.6 to determine a reflectance, a jitter and a modulation degree. The results were satisfactory; a reflectance: 50.0%, a jitter: 7.2% and a modulation degree: 0.64 in regeneration at 650 nm. The medium exhibited no changes after a light resistance test with a carbon arc for 100 hours and a humidity and heat-resistance test at 80° C. and 85% for 100 hours. Even after regeneration by 1 million cycles with a regenerating beam of 0.7 mW, the jitter varied only by 1% or less.

Furthermore, recording was performed with a linear velocity of 7.0 m/s (double-speed recording) and the shortest pit length of 0.40 μm, resulting in a recording sensitivity of 12.5 mW. After recording, a signal was regenerated using an evaluation device equipped with a 650 nm red semiconductor laser head with a lens numerical aperture of 0.6 to determine a reflectance, a jitter and a modulation degree. The results were satisfactory; a reflectance: 46.5%, a jitter: 8.0% and a modulation degree: 0.60 in regeneration at 650 nm.

EXAMPLE 12

An optical recording medium was prepared as described in Example 9, except that 0.10 g of the dipyrromethene-metal chelate compound (1-1) and 1.0 g of the dipyrromethene-metal chelate compound (4-1) were dissolved in 55 mL of. dimethylcyclohexane to prepare a dye solution.

Optical constants of this recording layer at 640 nm, 650 nm and 660 nm were as follows.

|   | 640 nm | 650 nm | 660 nm |
|---|--------|--------|--------|
| n | 2.45   | 2.31   | 2.20   |
| k | 0.15   | 0.09   | 0.07   |

As described in Example 6, on the optical recording medium thus prepared, recording was performed with a linear velocity of 3.5 m/s and the shortest pit length of 0.40 μm at a wavelength of 658 nm using an optical disc evaluator equipped with a semiconductor laser head whose lens numerical aperture was 0.6 (DDU-1000; PULSTEC INDUSTRIAL CO., LTD) and a pulse generator (PULSTEC INDUSTRIAL CO., LTD). A recording sensitivity was 11.0 m/W. After recording, a signal was regenerated using an evaluation device equipped with a 650 nm red semiconductor laser head with a lens numerical aperture of 0.6 to determine a reflectance, a jitter and a modulation degree. The results were satisfactory; a reflectance: 49.0%, a jitter: 7.2% and a modulation degree: 0.60 in regeneration at 650 nm. The medium exhibited no changes after a light resistance test with a carbon arc for 100 hours and a humidity and heat-resistance test at 80° C. and 85% for 100 hours. Even after regeneration by 1 million cycles with a regenerating beam of 0.7 mW, the jitter varied only by 1% or less.

Furthermore, recording was performed with a linear velocity of 7.0 m/s (double-speed recording) and the shortest pit length of 0.40 μm, resulting in a recording sensitivity of 12.5 mW. After recording, a signal was regenerated using an evaluation device equipped with a 650 nm red semiconductor laser head with a lens numerical aperture of 0.6 to determine a reflectance, a jitter and a modulation degree. The results were satisfactory; a reflectance: 46.5%, a jitter: 7.8% and a modulation degree: 0.61 in regeneration at 650 nm.

EXAMPLE 13

An optical recording medium was prepared as described in Example 9, except that 0.30 g of the dipyrromethene-metal chelate compound (1-1) and 0.70 g of the dipyrromethene-metal chelate compound (4-2) were dissolved in 50 mL of dimethylcyclohexane to prepare a dye solution.

Optical constants of this recording layer at 640 nm, 650 nm and 660 nm were as follows.

|   | 640 nm | 650 nm | 660 nm |
|---|--------|--------|--------|
| n | 2.63   | 2.31   | 2.24   |
| k | 0.32   | 0.14   | 0.07   |

On the optical recording medium thus prepared, recording was performed with a linear velocity of 3.5 m/s and the shortest pit length of 0.40 μm at a wavelength of 639 nm using an optical disc evaluator equipped with a semiconductor laser head whose lens numerical aperture was 0.6 (DDU-1000; PULSTEC INDUSTRIAL CO., LTD) and a pulse generator (PULSTEC INDUSTRIAL CO., LTD). A recording sensitivity was 10.0 m/W. After recording, a signal was regenerated using an evaluation device equipped with a 650 nm red semiconductor laser head with a lens numerical aperture of 0.6 to determine a reflectance, a jitter and a modulation degree. The results were satisfactory; a reflectance: 48.7%, a jitter: 7.7% and a modulation degree: 0.65 in regeneration at 650 nm. The medium exhibited no changes after a light resistance test with a carbon arc for 100 hours and a humidity and heat-resistance test at 80° C. and 85% for 100 hours. Even after regeneration by 1 million cycles with a regenerating beam of 0.7 mW, the jitter varied only by 1% or less.

Furthermore, recording was performed with a linear velocity of 7.0 m/s (double-speed recording) and the shortest pit length of 0.40 μm, resulting in a recording sensitivity of 13.5 mW. After recording, a signal was regenerated using an evaluation device equipped with a 650 nm red semiconductor laser head with a lens numerical aperture of 0.6 to determine a reflectance, a jitter and a modulation degree. The results were satisfactory; a reflectance: 46.0%, a jitter: 7.9% and a modulation degree: 0.61 in regeneration at 650 nm.

EXAMPLE 14

An optical recording medium was prepared as described in Example 9, except that 0.2 g of the dipyrromethene-metal chelate compound (1-11) was dissolved in 10 mL of dimethylcyclohexane to prepare a dye solution. Optical constants of this recording layer at 640 nm, 650 nm and 660 nm were as follows.

|   | 640 nm | 650 nm | 660 nm |
|---|--------|--------|--------|
| n | 2.56   | 2.38   | 2.27   |
| k | 0.22   | 0.12   | 0.08   |

As described in Example 9, on the optical recording medium thus prepared, recording was performed with a linear velocity of 3.5 m/s and the shortest pit length of 0.40 μm at a wavelength of 658 nm using an optical disc evaluator equipped with a semiconductor laser head whose lens numerical aperture was 0.6 (DDU-1000; PULSTEC INDUSTRIAL CO., LTD) and a pulse generator (PULSTEC INDUSTRIAL CO., LTD). A recording sensitivity was 8.5 m/W. After recording, a signal was regenerated using an evaluation device equipped with a 650 nm red semiconductor laser head with a lens numerical aperture of 0.6 to determine a reflectance, a jitter and a modulation degree. The results were satisfactory; a reflectance: 47.0%, a jitter: 7.4% and a modulation degree: 0.62 in regeneration at 650 nm. The medium exhibited no changes after a light resistance test with a carbon arc for 100 hours and a humidity and heat-resistance test at 80° C. and 85% for 100 hours. Even after regeneration by 1 million cycles with a regenerating beam of 0.7 mW, the jitter varied only by 1% or less.

Furthermore, recording was performed with a linear velocity of 7.0 m/s (double-speed recording) and the shortest pit length of 0.40 μm, resulting in a recording sensitivity of 13.0 mW. After recording, a signal was regenerated using an evaluation device equipped with a 650 nm red semiconductor laser head with a lens numerical aperture of 0.6 to determine a reflectance, a jitter and a modulation degree. The results were satisfactory; a reflectance: 46.5%, a jitter: 7.8% and a modulation degree: 0.60 in regeneration at 650 nm.

EXAMPLE 15

An optical recording medium was prepared as described in Example 9, except that 0.2 g of the dipyrromethene-metal chelate compound (1-48) was dissolved in 10 mL of dimethylcyclohexane to prepare a dye solution. Optical constants of this recording layer at 640 nm, 650 nm and 660 nm were as follows.

|   | 640 nm | 650 nm | 660 nm |
|---|--------|--------|--------|
| n | 2.56   | 2.40   | 2.28   |
| k | 0.14   | 0.08   | 0.06   |

As described in Example 9, on the optical recording medium thus prepared, recording was performed with a linear velocity of 3.5 m/s and the shortest pit length of 0.40 μm at a wavelength of 658 nm using an optical disc evaluator equipped with a semiconductor laser head whose lens numerical aperture was 0.6 (DDU-1000; PULSTEC INDUSTRIAL CO., LTD) and a pulse generator (PULSTEC INDUSTRIAL CO., LTD). A recording sensitivity was 9.5 m/W. After recording, a signal was regenerated using an evaluation device equipped with a 650 nm red semiconductor laser head with a lens numerical aperture of 0.6 to determine a reflectance, a jitter and a modulation degree. The results were satisfactory; a reflectance: 46.5%, a jitter: 7.6% and a modulation degree: 0.62 in regeneration at 650 nm. The medium exhibited no changes after a light resistance test with a carbon arc for 100 hours and a humidity and heat-resistance test at 80° C. and 85% for 100 hours. Even after regeneration by 1 million cycles with a regenerating beam of 0.7 mW, the jitter varied only by 1% or less.

Furthermore, recording was performed with a linear velocity of 7.0 m/s (double-speed recording) and the shortest pit length of 0.40 μm, resulting in a recording sensitivity of 14.0 mW. After recording, a signal was regenerated using an evaluation device equipped with a 650 nm red semiconductor laser head with a lens numerical aperture of 0.6 to determine a reflectance, a jitter and a modulation degree. The results were satisfactory; a reflectance: 45.0%, a jitter: 8.0% and a modulation degree: 0.66 in regeneration at 650 nm.

EXAMPLES 16 to 29

An optical recording medium was prepared and subject to recording evaluation with one-fold and two-fold speeds as described in Example 9, except using one of the dipyrromethene-metal chelate compounds listed in Table 1 alone or in combination with one of the dipyrromethene-metal chelate compounds listed in Table 2 as appropriate. Satisfactory results were indicated for all the parameters of sensitivity, a reflectance, a jitter and a modulation degree. The medium exhibited no changes after a light resistance test with a carbon arc for 100 hours and a humidity and heat-resistance test at 80° C. and 85% for 100 hours. Even after regeneration by 1 million cycles with a regenerating beam of 0.7 mW, the jitter varied only by 1% or less.

Comparative Example 1

An optical recording medium was prepared as described in Example 9 except that a solution of 0.2 g of the dipyrromethene-metal chelate compound (4-3) in 10 mL of dimethylcyclohexane was spin-coated.

On the medium thus prepared, recording was performed with a linear velocity of 3.5 m/s and the shortest pit length of 0.40 μm at a wavelength of 658 nm using an optical disc evaluator equipped with a semiconductor laser head whose lens numerical aperture was 0.6 (DDU-1000; PULSTEC INDUSTRIAL CO., LTD) and a pulse generator (PULSTEC INDUSTRIAL CO., LTD). A recording sensitivity was 9.5 m/W. After recording, a signal was regenerated using an evaluation device equipped with a 650 nm red semiconductor laser head to determine a reflectance, a jitter and a modulation degree. The results were as follows: a reflectance: 62%, a jitter: 20% or more and a modulation degree: 0.61 in regeneration at 650 nm. Thus, the jitter property was not satisfactory.

Furthermore, recording was evaluated with linear velocity of 7.0 m/s (double-speed recording) and the shortest pit length of 0.40 μm. As a result, a recording sensitivity was inadequate (>15 mW) for satisfactory recording.

Comparative Example 2

An optical recording medium was prepared as described in Example 9 except that a solution of 0.2 g of the dipyrromethene-metal chelate compound (4-1) in 10 mL of dimethylcyclohexane was spin-coated.

On the medium thus prepared, recording was performed with a linear velocity of 3.5 m/s and the shortest pit length of 0.40 μm at a wavelength of 658 nm using an optical disc evaluator equipped with a semiconductor laser head whose lens numerical aperture was 0.6 (DDU-1000; PULSTEC INDUSTRIAL CO., LTD) and a pulse generator (PULSTEC INDUSTRIAL CO., LTD). A recording sensitivity was 12.0 m/W. After recording, a signal was regenerated using an evaluation device equipped with a 650 nm red semiconductor laser head to determine a reflectance, a jitter and a modulation degree. The results were satisfactory: a reflectance: 46.5%, a jitter: 7.8% and a modulation degree: 0.60 in regeneration at 650 nm. The medium exhibited no changes after a light resistance test with a carbon arc for 100 hours and a humidity and heat-resistance test at 80° C. and 85% for 100 hours. Even after regeneration by 1 million cycles with a regenerating beam of 0.7 mW, the jitter varied only by 1% or less.

However, recording was evaluated with linear velocity of 7.0 m/s (double-speed recording) and the shortest pit length of 0.40 μm. As a result, a recording sensitivity was inadequate (>15 mW) for satisfactory recording.

Comparative Example 3

An optical recording medium was prepared as described in Example 9 except that a solution of 1 g of a pentamethinecyanine dye NK-2929, "1,3,3,1',3',3'-hexamethyl-2',2'-(4,5,4',1,5'-dibenzo)indodicarbocyanine perchlorate (Nippon Kanko Shikiso Kenkyusho), in 10 mL of dimethylcyclohexane was spin-coated.

On the medium thus prepared, recording was performed with a linear velocity of 3.5 m/s and the shortest pit length of 0.40 μm at a wavelength of 658 nm using an optical disc evaluator equipped with a semiconductor laser head whose lens numerical aperture was 0.6 (DDU-1000; PULSTEC INDUSTRIAL CO., LTD) and a pulse generator (PULSTEC INDUSTRIAL CO., LTD). A recording sensitivity was 10.0 m/W. After recording, a signal was regenerated using an evaluation device equipped with a 650 nm red semiconductor laser head to determine a reflectance, a jitter and a modulation degree. The results were not satisfactory: a reflectance: 10%, a jitter: 20% or more and a modulation degree: 0.14 in regeneration at 650 nm. After a light resistance test with a carbon arc for 100 hours, a signal was too deteriorated to be regenerated.

Furthermore, recording was evaluated with linear velocity of 7.0 m/s (double-speed recording) and the shortest pit length of 0.40 μm. As a result, a recording sensitivity was inadequate (>15 mW) for satisfactory recording.

Table 3 shows the optical constants for Examples 9 to 29 and Comparative Examples 1 to 3 together with the results for sensitivity, a reflectance, a jitter and a modulation degree when each optical recording medium was subject to recording and regeneration with normal and double speeds. In Table 3, a mixing ratio indicates a weight ratio of a dipyrromethene-metal compound giving a concentration of 20 g/L to dimethylcyclohexane. Recording was conducted at 658 nm except Examples 11 and 13.

EXAMPLE 30

On the medium prepared in Example 9, recording was performed with a linear velocity of 10.5 m/s (triple-speed recording) and the shortest pit length of 0.40 μm at a wavelength of 658 nm using an optical disc evaluator equipped with a semiconductor laser head whose lens numerical aperture was 0.6 (DDU-1000; PULSTEC INDUSTRIAL CO., LTD) and a pulse generator (PULSTEC INDUSTRIAL CO., LTD). A recording sensitivity was 13.5 m/W. After recording, a signal was regenerated using an evaluation device equipped with a 650 nm red semiconductor laser head (lens numerical aperture: 0.6) to determine a reflectance, a jitter and a modulation degree. The results were satisfactory: a reflectance: 46.0%, a jitter: 7.9% and a modulation degree: 0.61 in regeneration at 650 nm.

EXAMPLES 31 to 50

Triple-speed recording was performed as described in Example 30, using the optical recording media prepared in Examples 10 to 29 in place of the optical recording medium prepared in Example 9, to give satisfactory results for sensitivity, a reflectance, a jitter and a modulation degree.

Comparative Examples 4 to 6

Triple-speed recording was performed as described in Example 30, using the optical recording media prepared in Comparative Examples 1 to 3 in place of the optical recording medium prepared in Example 9, resulting in unsatisfactory recording due to a poor recording sensitivity (>15 mW).

Table 4 shows the results of sensitivity, a reflectance, a jitter and a modulation degree when each of the optical recording media in Examples 30 to 50 and Comparative Examples 4 to 6 was subject to recording and regeneration at triple-speed.

TABLE 3

| Example | Compd. 1 No. | Compd. 2 No. | Mixing Ratio | Optical Constant n/k (at 650 nm) | Recording at normal speed | | | | Recording at double speed | | | |
|---|---|---|---|---|---|---|---|---|---|---|---|---|
| | | | | | Sensitivity (mW) | Reflectivity (%) | Jitter (%) | Modulation Degree | Sensitivity (mW) | Reflectivity (%) | Jitter (%) | Modulation Degree |
| 9 | 1-1 | — | — | 2.39/0.14 | 9.5 | 49.5 | 7.5 | 0.60 | 13.5 | 45.5 | 7.9 | 0.60 |
| 10 | 1-4 | — | — | 2.41/0.12 | 9.5 | 47.4 | 7.7 | 0.63 | 13.0 | 46.0 | 8.0 | 0.60 |
| 11 | 1-8 | — | — | 2.18/0.05 | 9.5 | 50.0 | 7.2 | 0.64 | 12.5 | 46.5 | 8.0 | 0.60 |
| 12 | 1-1 | 4-1 | 1:10 | 2.31/0.09 | 11.0 | 49.0 | 7.2 | 0.60 | 12.5 | 46.5 | 7.8 | 0.61 |
| 13 | 1-1 | 4-2 | 3:7 | 2.31/0.14 | 10.0 | 48.7 | 7.7 | 0.65 | 13.5 | 46.0 | 7.9 | 0.61 |
| 14 | 1-11 | — | — | 2.38/0.12 | 8.5 | 47.0 | 7.4 | 0.62 | 13.0 | 46.5 | 7.8 | 0.60 |
| 15 | 1-48 | — | — | 2.40/0.08 | 9.5 | 46.5 | 7.6 | 0.62 | 14.0 | 45.0 | 8.0 | 0.66 |
| 16 | 1-46 | — | — | 2.38/0.12 | 8.5 | 47.0 | 7.4 | 0.59 | 11.5 | 47.0 | 7.2 | 0.62 |
| 17 | 1-47 | — | — | 2.52/0.15 | 7.5 | 45.0 | 7.3 | 0.60 | 10.5 | 43.0 | 7.9 | 0.66 |
| 18 | 1-54 | — | — | 2.22/0.10 | 9.5 | 50.1 | 7.2 | 0.61 | 13.0 | 46.5 | 7.8 | 0.63 |
| 19 | 1-55 | 4-8 | 1:9 | 2.35/0.12 | 12.0 | 49.0 | 7.2 | 0.60 | 13.5 | 48.9 | 7.8 | 0.61 |
| 20 | 1-68 | 4-8 | 2:8 | 2.19/0.11 | 10.0 | 48.7 | 7.7 | 0.64 | 12.5 | 46.0 | 7.9 | 0.62 |
| 21 | 1-69 | 4-5 | 3:7 | 2.21/0.09 | 8.5 | 47.0 | 8.0 | 0.65 | 13.0 | 46.5 | 7.6 | 0.60 |
| 22 | 1-79 | 4-1 | 3:7 | 2.22/0.08 | 10.0 | 48.0 | 6.9 | 0.61 | 11.5 | 46.9 | 8.0 | 0.66 |
| 23 | 1-80 | — | — | 2.18/0.09 | 9.5 | 46.7 | 7.9 | 0.60 | 13.6 | 45.4 | 7.7 | 0.65 |
| 24 | 1-81 | — | — | 2.21/0.11 | 8.5 | 46.5 | 7.8 | 0.61 | 11.5 | 46.8 | 7.9 | 0.60 |
| 25 | 1-82 | — | — | 2.23/0.12 | 9.5 | 45.8 | 7.2 | 0.66 | 12.0 | 46.5 | 7.3 | 0.65 |
| 26 | 1-91 | — | — | 2.36/0.12 | 7.6 | 46.1 | 7.7 | 0.62 | 11.0 | 45.9 | 7.5 | 0.65 |
| 27 | 1-92 | — | — | 2.30/0.14 | 7.5 | 45.6 | 7.4 | 0.60 | 11.5 | 46.0 | 7.5 | 0.63 |
| 28 | 1-93 | — | — | 2.38/0.11 | 8.3 | 46.5 | 7.4 | 0.61 | 12.1 | 46.1 | 7.6 | 0.62 |
| 29 | 1-108 | — | — | 2.31/0.12 | 8.5 | 46.8 | 7.7 | 0.62 | 12.5 | 45.8 | 7.5 | 0.62 |
| Comp. Ex. 1 | — | 4-3 | — | 2.02/0.04 | 9.5 | 62.0 | >20.0 | 0.61 | >15.0 | — | — | — |
| Comp. Ex. 2 | — | 4-1 | — | 2.30/0.08 | 12.0 | 46.5 | 7.8 | 0.60 | >15.0 | — | — | — |
| Comp. Ex. 3 | NK2929 | — | — | 1.78/1.22 | 10.0 | 10.0 | >20.0 | 0.14 | >15.0 | — | — | — |

TABLE 4

| | | | | Recording at triple-speed | | | |
|---|---|---|---|---|---|---|---|
| Ex. | Compd. 1 No. | Compd. 2 No. | Mixing Ratio | Sensitivity (mW) | Reflectivity (%) | Jitter (%) | Modulation Degree |
| 30 | 1-1 | — | — | 13.5 | 46.0 | 7.9 | 0.61 |
| 31 | 1-4 | — | — | 13.0 | 47.4 | 7.6 | 0.63 |
| 32 | 1-8 | — | — | 13.0 | 50.0 | 8.0 | 0.60 |
| 33 | 1-1 | 4-1 | 1:10 | 12.7 | 49.0 | 7.7 | 0.61 |
| 34 | 1-1 | 4-2 | 3:7 | 13.8 | 48.7 | 7.7 | 0.61 |
| 35 | 1-11 | — | — | 13.0 | 47.0 | 6.9 | 0.62 |
| 36 | 1-48 | — | — | 13.5 | 46.5 | 8.0 | 0.65 |
| 37 | 1-46 | — | — | 11.5 | 47.0 | 7.5 | 0.62 |
| 38 | 1-47 | — | — | 10.5 | 45.0 | 7.5 | 0.66 |
| 39 | 1-54 | — | — | 12.0 | 50.1 | 7.6 | 0.65 |
| 40 | 1-55 | 4-8 | 1:9 | 12.0 | 49.0 | 7.4 | 0.64 |
| 41 | 1-68 | 4-8 | 2:8 | 13.0 | 48.7 | 6.9 | 0.61 |
| 42 | 1-69 | 4-5 | 3:7 | 13.5 | 47.0 | 7.0 | 0.62 |
| 43 | 1-79 | 4-1 | 3:7 | 11.5 | 48.0 | 8.0 | 0.65 |
| 44 | 1-80 | — | — | 13.8 | 46.7 | 7.7 | 0.64 |
| 45 | 1-81 | — | — | 12.0 | 46.5 | 7.5 | 0.60 |
| 46 | 1-82 | — | — | 12.4 | 45.8 | 7.3 | 0.64 |
| 47 | 1-91 | — | — | 11.5 | 46.1 | 6.8 | 0.68 |
| 48 | 1-92 | — | — | 12.5 | 45.6 | 7.8 | 0.67 |
| 49 | 1-93 | — | — | 12.5 | 46.5 | 7.7 | 0.66 |
| 50 | 1-108 | — | — | 13.0 | 46.8 | 7.8 | 0.67 |
| Comp. Ex.4 | — | 4-3 | — | >15.0 | — | — | — |
| Comp. Ex.5 | — | 4-1 | — | >15.0 | — | — | — |
| Comp. Ex.6 | NK2929 | — | — | >15.0 | — | — | — |

What is claimed is:

1. An optical recording medium comprising at least a recording layer and a reflecting layer on a substrate wherein the recording layer contains at least one dipyrromethene-metal chelate compound represented by general formula (1):

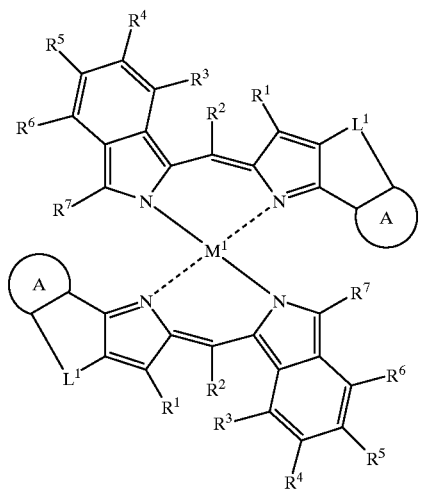

(1)

wherein $R^1$ to $R^6$ independently represent hydrogen, halogen, nitro, cyano, hydroxyl, amino, carboxyl, sulfo, substituted or unsubstituted alkyl with up to 20 carbon atoms, alkoxy, alkylthio, aryloxy, arylthio, alkenyl, acyl, alkoxycarbonyl, carbamoyl, acylamino, aralkyl, aryl or heteroaryl; $R^7$ represents halogen, aryl, heteroaryl, alkoxy, alkylthio, aryloxy or arylthio; A represents substituted or unsubstituted aromatic or heterocyclic ring with up to 20 carbon atoms; $L^1$ represents substituted or unsubstituted bivalent residue forming a ring together with carbon atoms to which it attaches and optionally containing a hetero atom; and $M^1$ represents transition metal element.

2. The optical recording medium as claimed in claim 1 wherein the dipyrromethene-metal chelate compound is the dipyrromethene-metal chelate compound represented by general formula (2):

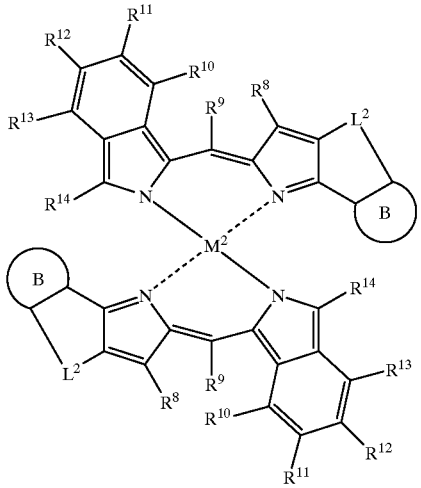

(2)

wherein $R^8$ to $R^{18}$ independently represent hydrogen, halogen, nitro, cyano, hydroxyl, amino, carboxyl, sulfo, substituted or unsubstituted alkyl with up to 20 carbon atoms, alkoxy, alkylthio, aryloxy, arylthio, alkenyl, acyl, alkoxycarbonyl, carbamoyl, acylamino, aralkyl, aryl or heteroaryl; $R^{14}$ represents halogen, aryl, heteroaryl, alkoxy, alkylthio, aryloxy or arylthio; B represents substituted or unsubstituted aromatic or heterocyclic ring with up to 20 carbon atoms; $L^2$ represents substituted or unsubstituted alkylene residue forming a ring together with carbon atoms to which it attaches; and $M^2$ represents transition metal element.

3. The optical recording medium as claimed in claim 2 wherein the dipyrromethene-metal chelate compound is the dipyrromethene-metal chelate compound represented by general formula (3):

(3)

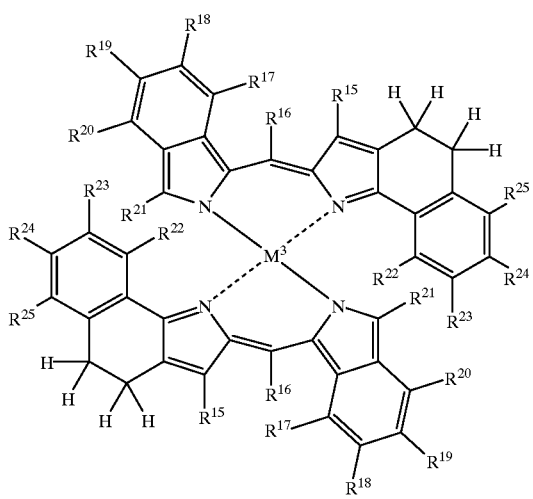

wherein $R^{15}$ to $R^{20}$, $R^{22}$ to $R^{25}$ independently represent hydrogen, halogen, nitro, cyano, hydroxyl, amino, carboxyl, sulfo, substituted or unsubstituted alkyl with up to 20 carbon atoms, alkoxy, alkylthio, aryloxy, arylthio, alkenyl, acyl, alkoxycarbonyl, carbamoyl, acylamino, aralkyl, aryl or heteroaryl; $R^{21}$ represents halogen, substituted or unsubstituted aryl with up to 20 carbon atoms; heteroaryl alkoxy, alkylthio, aryloxy or arylthio; $M^3$ represents transition metal element.

4. The optical recording medium as claimed in claim 1 wherein $R^1$ in general formula (1) is halogen.

5. The optical recording medium as claimed in claim 2 wherein $R^8$ in general formula (2) is halogen.

6. The optical recording medium as claimed in claim 3 wherein $R^{15}$ in general formula (3) is halogen.

7. The optical recording medium as claimed in claim 1 wherein the recording layer further contains at least one dipyrromethene-metal chelate compound represented by general formula (4):

(4)

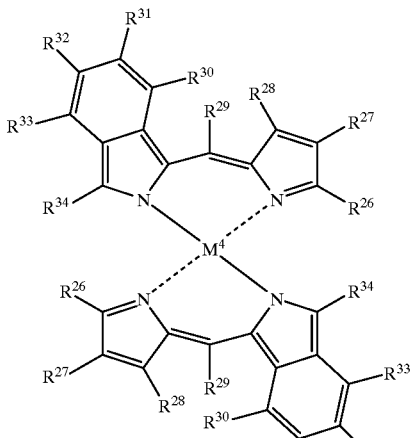

wherein $R^{26}$ to $R^{33}$ independently represent hydrogen, halogen, nitro, cyano, hydroxyl, amino, carboxyl, sulfo, substituted or unsubstituted alkyl with up to 20 carbon atoms, alkoxy, alkylthio, aryloxy, arylthio, alkenyl, acyl, alkoxycarbonyl, carbamoyl, acylamino, aralkyl, aryl or heteroaryl; $R^{34}$ represents halogen, substituted or unsubstituted aryl with up to 20 carbon atoms, heteroaryl, alkoxy, alkylthio, aryloxy or arylthio; and $M^4$ represents transition metal element.

8. The optical recording medium as claimed in claim 2 wherein the recording layer further contains at least one dipyrromethene-metal chelate compound represented by general formula (4):

(4)

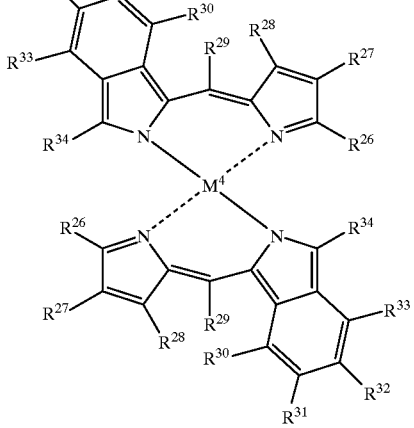

wherein $R^{26}$ to $R^{33}$ independently represent hydrogen, halogen, nitro, cyano, hydroxyl, amino, carboxyl, sulfo, substituted or unsubstituted alkyl with up to 20 carbon atoms, alkoxy, alkylthio, aryloxy, arylthio, alkenyl, acyl, alkoxycarbonyl, carbamoyl, acylamino, aralkyl, aryl or heteroaryl; $R^{34}$ represents halogen, substituted or unsubstituted aryl with up to 20 carbon atoms, heteroaryl, alkoxy, alkylthio, aryloxy or arylthio; and $M^4$ represents transition metal element.

9. The optical recording medium as claimed in claim 3 wherein the recording layer further contains at least one dipyrromethene-metal chelate compound represented by general formula (4):

(4)

wherein $R^{26}$ to $R^{33}$ independently represent hydrogen, halogen, nitro, cyano, hydroxyl, amino, carboxyl, sulfo, substituted or unsubstituted alkyl with up to 20 carbon atoms, alkoxy, alkylthio, aryloxy, arylthio, alkenyl, acyl, alkoxycarbonyl, carbamoyl, acylamino, aralkyl, aryl or heteroaryl; $R^{34}$ represents halogen, substituted or unsubstituted aryl with up to 20 carbon atoms, heteroaryl, alkoxy, alkylthio, aryloxy or arylthio; and $M^4$ represents transition metal element.

10. The optical recording medium as claimed in claim 1 wherein the recording layer has a refractive index of at least 1.8 at a laser wavelength and an extinction coefficient of 0.04 to 0.40.

11. The optical recording medium as claimed in claim 2 wherein the recording layer has a refractive index of at least 1.8 at a laser wavelength and an extinction coefficient of 0.04 to 0.40.

12. The optical recording medium as claimed in claim 3 wherein the recording layer has a refractive index of at least 1.8 at a laser wavelength and an extinction coefficient of 0.04 to 0.40.

13. The optical recording medium as claimed in claim 4 wherein the recording layer has a refractive index of at least 1.8 at a laser wavelength and an extinction coefficient of 0.04 to 0.40.

14. The optical recording medium as claimed in claim 5 wherein the recording layer has a refractive index of at least 1.8 at a laser wavelength and an extinction coefficient of 0.04 to 0.40.

15. The optical recording medium as claimed in claim 6 wherein the recording layer has a refractive index of at least 1.8 at a laser wavelength and an extinction coefficient of 0.04 to 0.40.

16. The optical recording medium as claimed in claim 7 wherein the recording layer has a refractive index of at least 1.8 at a laser wavelength and an extinction coefficient of 0.04 to 0.40.

17. The optical recording medium as claimed in claim 8 wherein the recording layer has a refractive index of at least 1.8 at a laser wavelength and an extinction coefficient of 0.04 to 0.40.

18. The optical recording medium as claimed in claim 9 wherein the recording layer has a refractive index of at least 1.8 at a laser wavelength and an extinction coefficient of 0.04 to 0.40.

19. The optical recording medium as claimed in claim 1 wherein recording and regenerating can be performed for a laser beam with a wavelength within a range of 520 to 690.

20. The optical recording medium as claimed in claim 2 wherein recording and regenerating can be performed for a laser beam with a wavelength within a range of 520 to 690.

21. The optical recording medium as claimed in claim 3 wherein recording and regenerating can be performed for a laser beam with a wavelength within a range of 520 to 690.

22. The optical recording medium as claimed in claim 4 wherein recording and regenerating can be performed for a laser beam with a wavelength within a range of 520 to 690.

23. The optical recording medium as claimed in claim 5 wherein recording and regenerating can be performed for a laser beam with a wavelength within a range of 520 to 690.

24. The optical recording medium as claimed in claim 6 wherein recording and regenerating can be performed for a laser beam with a wavelength within a range of 520 to 690.

25. The optical recording medium as claimed in claim 7 wherein recording and regenerating can be performed for a laser beam with a wavelength within a range of 520 to 690.

26. The optical recording medium as claimed in claim 8 wherein recording and regenerating can be performed for a laser beam with a wavelength within a range of 520 to 690.

27. The optical recording medium as claimed in claim 9 wherein recording and regenerating can be performed for a laser beam with a wavelength within a range of 520 to 690.

28. A dipyrromethene-metal chelate compound represented by general formula (1):

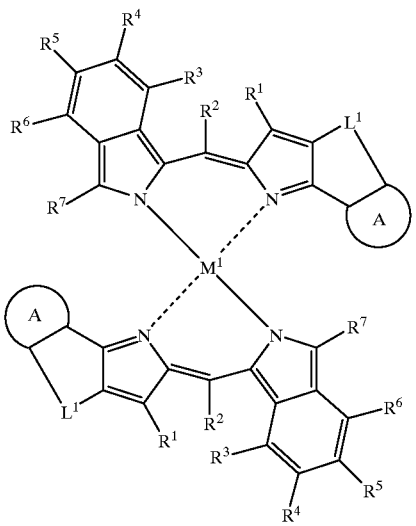

(1)

wherein $R^1$ to $R^6$ independently represent hydrogen, halogen, nitro, cyano, hydroxyl, amino, carboxyl, sulfo, substituted or unsubstituted alkyl with up to 20 carbon atoms, alkoxy, alkylthio, aryloxy, arylthio, alkenyl, acyl, alkoxycarbonyl, carbamoyl, acylamino, aralkyl, aryl or heteroaryl; $R^7$ represents halogen, aryl, heteroaryl, alkoxy, alkylthio, aryloxy or arylthio; A represents substituted or unsubstituted aromatic or heterocyclic ring with up to 20 carbon atoms; $L^1$ represents substituted or unsubstituted bivalent residue forming a ring together with carbon atoms to which it attaches and optionally containing a hetero atom; and $M^1$ represents transition metal element.

29. The dipyrromethene-metal chelate compound as claimed in claim 28 represented by general formula (2):

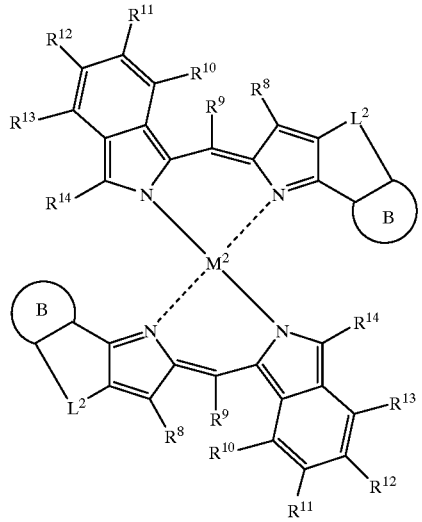

(2)

wherein $R^8$ to $R^{13}$ independently represent hydrogen, halogen, nitro, cyano, hydroxyl, amino, carboxyl, sulfo, substituted or unsubstituted alkyl with up to 20 carbon atoms, alkoxy, alkylthio, aryloxy, arylthio, alkenyl, acyl, alkoxycarbonyl, carbamoyl, acylamino, aralkyl, aryl or heteroaryl; $R^{14}$ represents halogen, aryl, heteroaryl, alkoxy, alkylthio, aryloxy or arylthio; B represents substituted or unsubstituted aromatic or heterocyclic ring with up to 20 carbon atoms; $L^2$ represents substituted or unsubstituted alkylene residue forming a ring together with carbon atoms to which it attaches; and $M^2$ represents transition metal element.

30. The dipyrromethene-metal chelate compound as claimed in claim 29 represented by general formula (3):

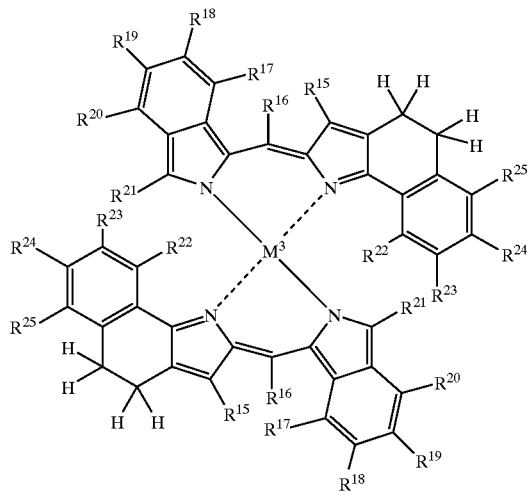

(3)

wherein $R^{15}$ to $R^{20}$, $R^{22}$ to $R^{25}$ independently represent hydrogen, halogen, nitro, cyano, hydroxyl, amino, carboxyl, sulfo, substituted or unsubstituted alkyl with up to 20 carbon atoms, alkoxy, alkylthio, aryloxy, arylthio, alkenyl, acyl, alkoxycarbonyl, carbamoyl, acylamino, aralkyl, aryl or heteroaryl; $R^{21}$ represents halogen, substituted or unsubstituted aryl with up to 20 carbon atoms, heteroaryl, alkoxy, alkylthio, aryloxy or arylthio; $M^3$ represents transition metal element.

31. The dipyrromethene-metal chelate compound as claimed in claim 28 wherein $R^1$ in general formula (1) is halogen.

32. The dipyrromethene-metal chelate compound as claimed in claim 29 wherein $R^8$ in general formula (2) is halogen.

33. The dipyrromethene-metal chelate compound as claimed in claim 30 wherein $R^{15}$ in general formula (3) is halogen.

* * * * *